(12) United States Patent
Dinnell et al.

(10) Patent No.: US 6,476,045 B2
(45) Date of Patent: Nov. 5, 2002

(54) AZAINDOLE DERIVATIVES AND THEIR USE AS THERAPEUTIC AGENTS

(75) Inventors: Kevin Dinnell, Much Hadham (GB); Jason Matthew Elliott, Felsted (GB); Gregory John Hollingworth, Brentwood (GB); Duncan Edward Shaw, Bishops Stortford (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/903,108

(22) Filed: Jul. 11, 2001

(65) Prior Publication Data

US 2002/0022624 A1 Feb. 21, 2002

(30) Foreign Application Priority Data

Jul. 13, 2000 (GB) .............................................. 0017256

(51) Int. Cl.$^7$ .................... C07D 401/06; C07D 401/10; A61K 31/454
(52) U.S. Cl. ........................ 514/300; 514/303; 514/322; 514/323; 514/256; 514/278; 546/113; 546/118; 546/121; 546/199; 546/200; 546/16; 546/17; 544/231
(58) Field of Search ................................. 546/113, 121, 546/118, 199, 201; 514/300, 303, 322, 323

(56) References Cited

U.S. PATENT DOCUMENTS 6,071,927 A 6/2000 Baker et al.
2001/0039286 A1 11/2001 Dinnell

FOREIGN PATENT DOCUMENTS

| EP | 0 655 442 | 5/1995 |
|---|---|---|
| GB | 2 311 523 | 10/1997 |
| WO | WO 99/21553 | 5/1999 |
| WO | WO 99/21557 | 5/1999 |
| WO | WO 00/51984 | 9/2000 |
| WO | WO 00/56727 | 9/2000 |

*Primary Examiner*—Deepak R. Rao
(74) *Attorney, Agent, or Firm*—J. Eric Thies; Melvin Winokur

(57) ABSTRACT

The present invention relates to compounds of the formula (I):

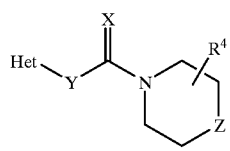

wherein:

Het represents a heterocyclic residue selected from:

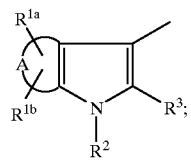

(a)

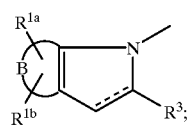

(b)

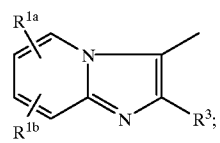

(c)

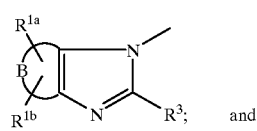

(d) and

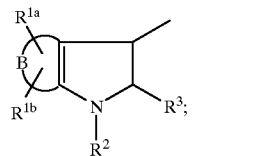

(e)

where the dotted line in (b) represents an optional double bond;
A completes a fused pyridine ring; and
B completes a fused benzene or pyridine ring.

The compounds are of particular use in the treatment or prevention of depression, anxiety, pain, inflammation, migaine, emesis or postherpetic neuralgia.

29 Claims, No Drawings

AZAINDOLE DERIVATIVES AND THEIR USE AS THERAPEUTIC AGENTS

This invention relates to indole and azaindole derivatives and their use as tachykinin antagonists, and in particular as neurokinin-1 receptor antagonists.

We have now found a class of indole and azaindole derivatives which are potent receptor antagonists of tachykinins, especially of the neurokinin-1 (substance P) receptor.

The present invention accordingly provides the compounds of the formula (I):

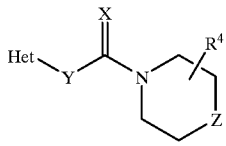

I wherein:
Het represents a heterocyclic residue selected from:

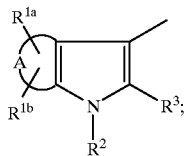

(a)

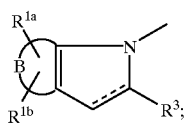

(b)

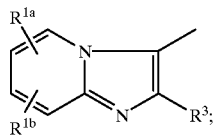

(c)

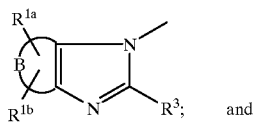

(d) and

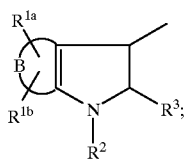

(e)

where the dotted line in (b) represents an optional double bond;
A completes a fused pyridine ring;
B completes a fused benzene or pyridine ring;
X represents an oxygen atom, a sulfur atom, two hydrogen atoms, =NH or =N($C_{1-6}$alkyl);
Y is a straight or branched $C_{1-4}$alkylene chain optionally substituted by halogen, oxo or hydroxy; or Y represents a straight or branched $C_{2-4}$alkenylene or $C_{2-4}$alkynylene chain;

Z represents $CR^5R^6$ or $NR^7$ so as to complete a piperidine or piperazine ring;
$R^{1a}$ and $R^{1b}$ each independently represent hydrogen, $C_{1-6}$alkyl, $C_{2-6}$alkenyl, $C_{1-6}$alkoxy, fluoro$C_{1-6}$alkyl, fluoro$C_{1-6}$alkoxy, halogen, cyano, $NR^aR^b$, $SR^a$, $SOR^a$, $SO_2R^a$, $OSO_2R^a$, $NR^aCOR^b$, $COR^a$, $CO_2R^a$ or $CONR^aR^b$;
$R^2$ represents hydrogen, $C^{1-6}$alkyl, fluoro$C_{1-6}$alkyl, $(CH_2)_m COR^a$, $(CH_2)_p CO_2R^a$, $(CH_2)_p OH$, $(CH_2)_m CONR^aR^b$, $(CH_2)_m$phenyl or $SO_2C_{1-6}$alkyl;
$R^3$ represents phenyl, biphenyl, naphthyl or heteroaryl, wherein said phenyl, biphenyl, naphthyl or heteroaryl group may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl or —O$(CH_2)_{1-2}$O—;
$R^4$ represents hydrogen, $C_{1-6}$alkyl, carbonyl (=O), $(Ch_2)_p$ phenyl or a $C_{1-2}$alkylene bridge across the piperidine or piperazine ring;
$R^5$ and $R^6$ each independently represent hydrogen, halogen, $C_{1-6}$alkyl, $C_{3-7}$cycloalkyl, $C_{3-7}$cycloalkyl$C_{1-4}$alkyl, $C_{2-6}$alkenyl, cyano, naphthyl, fluorenyl, $(CH_2)_m$phenyl, $(CH_2)_m$heteroaryl, CH(phenyl)$_2$, CH($C_{1-6}$alkyl)(phenyl), C($C_{1-6}$alkyl)(phenyl)$_2$, CO(phenyl), C(OH)(phenyl)$_2$, $C_{2-4}$alkenyl(phenyl), $(CH_2)_m NR^cR^d$, $(CH_2)_p CONR^cR^d$, $(CH_2)_p NR^aCOR^b$, $(CH_2)_m COR^c$, $(CH_2)_m CO_2R^c$ or $(CH_2)_m OH$ wherein said phenyl, naphthyl, fluorenyl or heteroaryl groups may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl or —O$(CH_2)_{1-2}$O—; or $R^5$ and $R^6$ together are linked so as to form a 5- or 6-membered ring optionally substituted by =O, =S or a $C_{1-4}$alkyl or hydroxy group, and optionally containing a double bond, which ring may optionally contain in the ring one or two heteroatoms selected from O and S, or groups selected from $NR^c$, SO or $SO_2$, and to which ring there is either fused or attached a benzene or thiophene ring, which benzene or thiophene ring is optionally substituted by 1, 2 or 3 substituents selected from $C_{1-6}$alkyl, $C_{3-7}$cycloalkyl, $C_{3-7}$cycloalkyl$C_{1-4}$alkyl, phenyl$C_{1-4}$alkyl, trifluoromethyl, cyano, $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$ or $CONR^aR^b$, wherein the phenyl moiety of a phenyl$C_{1-4}$alkyl group may be substituted by $C_{1-6}$alkyl, $C_{1-6}$alkoxy, halogen or trifluoromethyl;
$R^7$ represents $C_{1-6}$alkyl, $C_{3-7}$cycloalkyl, $C_{3-7}$cycloalkyl$C_{1-4}$alkyl, $C_{2-6}$alkenyl, $(CH_2)_m$phenyl, naphthyl, fluorenyl, $(CH_2)_m$heteroaryl, CH(phenyl)$_2$, CH($C_{1-6}$alkyl)(phenyl), $C_{2-4}$alkenyl(phenyl), $(CH_2)_p NR^cR^d$, $(CH_2)_m CONR^cR^d$, $(CH_2)_m COR^c$, $(CH_2)_m CO_2R^c$ or $(CH_2)_p OH$, where said phenyl, naphthyl, fluorenyl or heteroaryl groups may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl or —O$(CH_2)_{1-2}$O—;
$R^a$ and $R^b$ each independently represents hydrogen, $C_{1-4}$alkyl, fluoro$C_{1-4}$alkyl or phenyl; or the group —$NR^aR^b$ may form a 5- or 6-membered ring optionally substituted by =O, =S or a $C_{1-4}$alkyl or hydroxy group, and optionally containing a double bond, which ring may optionally contain in the ring one or two heteroatoms selected from O and S, or groups selected from $NR^c$, SO or $SO_2$;
$R^c$ and $R^d$ each independently represents hydrogen, $C_{1-4}$alkyl, fluoro$C_{1-4}$alkyl, $C_{2-4}$alkenyl, $COR^a$, $SO_2R^a$, phenyl or benzyl or $R^c$ and $R^d$, together with the nitrogen atom to which they are attached, form a heteroaliphatic ring of 4 to 7 atoms, to which ring there may optionally be fused a benzene ring;

m is zero or an integer from 1 to 4;

p is an integer from 1 to 4;

or a pharmaceutically acceptable salt thereof.

In the heterocyclic residues (a)–(e) represented by "Het", pyridine rings completed by A or B may be fused to the 5-membered rings in any of the possible orientations. Thus, for example, (a) may represent a pyrrolo[2,3-b]pyridine system, a pyrrolo[2,3-C]pyridine system, a pyrrolo[3,2-c] pyridine system, or a pyrrolo[3,2-b]pyridine system.

In a subgroup of the compounds of formula I, B completes a fused benzene ring.

In another subgroup of the compounds of formula I, when Het represents (b), a double bond is present in the position indicated by the dotted line.

A preferred group of compounds of formula I is that wherein $R^{1a}$ and $R^{1b}$ each independently represent hydrogen, halogen, $C_{1-6}$alkyl, $C_{2-6}$alkenyl, fluoro$C_{1-6}$alkoxy, $NR^aR^b$, $COR^a$, $CO_2R^a$, or heteroaryl. When $R^{1a}$ and $R^{1b}$ are both other than hydrogen, preferably $R^{1a}$ and $R^{1b}$ are the same. When $R^{1a}$ is other than hydrogen and $R^{1b}$ is hydrogen, $R^{1a}$ is preferably attached to the 5-position when Het represents (a) or (e), to the 5- or 6-position when Het represents (b) or (d), and to the 6-position when Het represents (c).

A particularly preferred group of compounds of formula (I) is that wherein $R^{1a}$ and $R^{1b}$ each independently represent hydrogen, methyl, vinyl, trifluoromethoxy, fluorine, chlorine, bromine, pyrrolidinyl, piperidinyl, morpholino, acetyl, methoxycarbonyl, pyridyl (especially 3-pyridyl) or furyl (especially 2-furyl).

An especially preferred group of compounds of formula (I) is that wherein $R^{1a}$ represents methyl or chloro, and $R^{1b}$ is hydrogen.

A subclass of compounds of formula (I) is that wherein Het represents (a) or (e). Within this subclass, a preferred group of compounds is that wherein $R^2$ represents hydrogen, $C_{1-6}$alkyl, fluoro$C_{1-6}$alkyl, $(CH_2)_mCOR^a$, $(CH_2)_pCOR^a$, $(CH_2)_pOH$ or $(CH_2)_m$phenyl. More preferably, $R^2$ represents $C_{1-3}$alkyl (especially methyl, ethyl or isopropyl), fluoro$C_{1-3}$alkyl (especially trifluoromethyl or 2,2,2-trifluoroethyl), $COCH_3$, $CH_2CO_2H$, $CH_2CO_2CH_3$, $(CH_2)_{1-2}OH$ (especially $CH_2CH_2OH$) or benzyl. An especially preferred group of compounds within this subclass is that wherein $R^2$ is hydrogen or methyl.

Another preferred group of compounds of formula (I) is that wherein $R^3$ represents phenyl, biphenyl, naphthyl (especially 2-naphthyl) or heteroaryl (especially 2- or 3-pyridyl) wherein said phenyl, biphenyl, naphthyl or heteroaryl group is optionally substituted by one or two groups selected from halogen, $C_{1-6}$alkyl, $C_{1-6}$alkoxy, trifluoro$C_{1-6}$alkyl, fluoro$C_{1-6}$alkoxy or $C_{2-6}$alkenyl.

A particularly preferred class of compounds of formula (I) is that wherein $R^3$ represents phenyl, biphenyl, naphthyl (especially 2-naphthyl) or heteroaryl (especially 2- or 3-pyridyl) wherein said phenyl, biphenyl, naphthyl or heteroaryl group is optionally substituted by one or two groups selected from fluorine, chlorine, bromine, $C_{1-4}$alkyl (especially methyl, isopropyl or tertiary butyl), methoxy, trifluoromethyl, trifluoromethoxy or vinyl.

An especially preferred group of compounds of formula (I) is that wherein $R^3$ represents 2-pyridyl, 3-pyridyl or phenyl optionally substituted by one or two groups selected from fluorine, chlorine, bromine, $C_{1-4}$alkyl (especially methyl, isopropyl or tertiary butyl), methoxy, trifluoromethyl, trifluoromethoxy or vinyl.

A most especially preferred class of compounds of formula (I) is that wherein $R^3$ represents phenyl, 4-methylphenyl, 4-chlorophenyl, 4-bromophenyl, 4-fluorophenyl, 2-pyridyl or 3-pyridyl.

A further preferred group of compounds of formula (I) is that wherein $R^4$ represents hydrogen, methyl, carbonyl, benzyl or a methylene bridge across the 2,5-positions on the piperidine or piperazine ring.

As especially preferred group of compounds of formula (I) is that wherein $R^4$ is hydrogen.

In a subclass of the compounds of formula (I), Z represents $CR^5R^6$. Within this subclass, a preferred group of compounds is that wherein $R^5$ represents halogen, $C_{3-7}$cycloalkyl, $C_{3-7}$cycloalkyl$C_{1-4}$alkyl, phenyl, heteroaryl, $(CH_2)_p$phenyl, $(CH_2)_p$heteroaryl, $CH(phenyl)_2$, $CH(C_{1-6}alkyl)(phenyl)$, $C(C_{1-6}alkyl)(phenyl)_2$, $CO(phenyl)$, $C(OH)(phenyl)_2$, or $(CH_2)_pNR^cR^d$, wherein said phenyl or heteroaryl group is optionally substituted by one or two substituents selected from halogen, $C_{1-6}$alkyl, $C_{1-6}$alkoxy, fluoro$C_{1-6}$alkyl, fluoro$C_{1-6}$alkoxy, $NO_2$, cyano, $SR^a$ or $—O(CH_2)_{1-2}O—$.

A particularly preferred group of compounds in this subclass is that wherein $R^5$ represents $C_{5-7}$cycloalkyl (especially cyclohexyl), phenyl, heteroaryl, $(CH_2)_p$phenyl (especially wherein p is 1 or 2), $CO(p-methoxyphenyl)$, $C(OH)(phenyl)_2$, or $(CH_2)_pNR^cR^d$ (especially where $R^c$ and $R^d$ each independently represent hydrogen, $C_{1-4}$alkyl, $C_{2-4}$alkenyl, $COR^a$ (especially wherein $R^a$ is methyl or ethyl), $SO_2R^a$ (especially wherein $R^a$ is methyl), phenyl or benzyl, or $R^c$ and $R^d$, together with the nitrogen atom to which they are attached, form a piperidine ring; and especially wherein p is zero or 1), wherein each of said phenyl or heteroaryl groups may be substituted by one or two groups independently selected from halogen, $C_{1-4}$alkyl, $C_{1-4}$alkoxy, fluoro$C_{1-4}$alkyl, fluoro$C_{1-4}$alkoxy, $NO_2$, cyano and $SO_2R^a$ (especially wherein $R^a$ represents $C_{1-4}$alkyl), or said phenyl or heteroaryl group may be substituted by the group $—O(CH_2)_{1-2}O—$. Particularly preferred are compounds in which said phenyl groups are unsubstituted or substituted by one or two substituents independently selected from fluorine, chlorine, methyl, ethyl, methoxy, ethoxy, isopropoxy, trifluoromethoxy, nitro, cyano and thiomethyl, or said phenyl is substituted by $—OCH_2O—$. Also preferred are compounds in which said heteroaryl groups are unsubstituted or are monosubstituted by methyl or trifluoromethyl.

Another preferred group of compounds within this subclass is that wherein $R^6$ represents hydrogen, fluorine, cyano, $(CH_2)_mNR^cR^d$, $(CH_2)_pNR^aCOR^b$, $(CH_2)_mCO_2R^c$ or $(CH_2)_mOH$, where $R^a$, $R^b$, $R^c$ and $R^d$ are as previously defined.

Particularly preferred are compounds wherein $R^6$ represents hydrogen, cyano, $NR^cR^d$ (especially wherein $R^c$ and $R^d$ are both $C_{1-3}$alkyl, most especially methyl), $CH_2NHCOR^b$ (especially wherein $R^b$ is $C_{1-3}$alkyl, most especially methyl), $CO_2R^c$ (especially wherein $R^c$ is hydrogen or $C_{1-3}$alkyl, most especially hydrogen or methyl), or $(CH_2)_mOH$ (especially where m is zero or 1).

Very aptly, $R^5$ represents benzyl and $R^6$ represents OH.

Where $R^5$ and $R^6$ are taken together there is preferably formed a 5- or 6-membered ring optionally substituted by $=O$ or a hydroxy group, and optionally containing a double bond, which ring optionally contains in the ring an oxygen or sulfur atom or 1 or 2 NH groups, and to which ring is either fused or attached a benzene ring, which benzene ring is optionally substituted by $C_{1-3}$alkyl or $SO_2R^a$, where $R^a$ is as previously defined.

In particular, when $R^5$ and $R^6$ are so linked as to form a 5- or 6-membered ring, suitable definitions of the $CR^5R^6$ moiety are selected from:

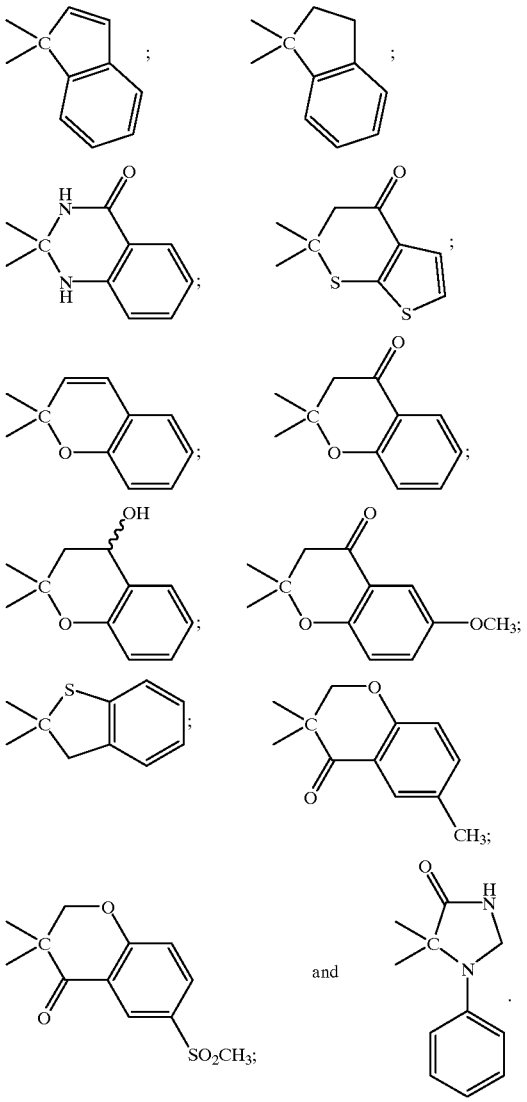

Particularly preferred examples of the $CR^5R^6$ moiety are selected from:

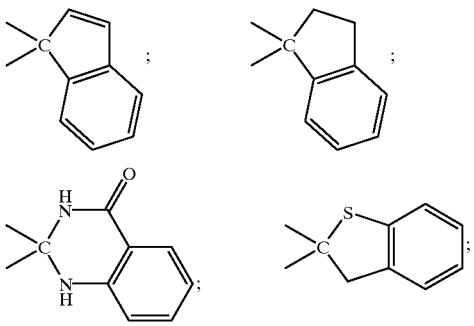

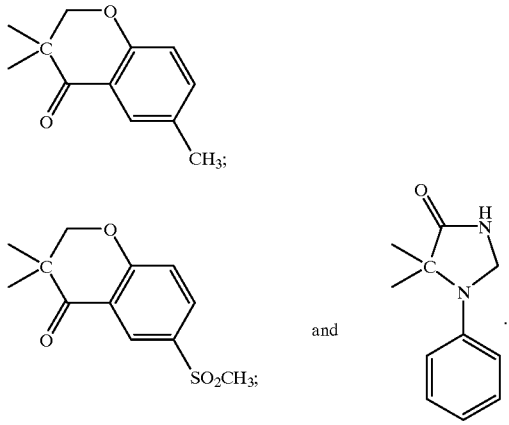

In a further subclass of the compounds of formula (I), Z represents $NR^7$. Within this subclass, a preferred group of compounds is that wherein $R^7$represents $C_{1-6}$alkyl, $C_{3-7}$cycloalkyl, $C_{3-7}$cycloalkyl$C_{1-4}$alkyl, $C_{2-6}$alkenyl, naphthyl, fluorenyl, $(CH_2)_m$phenyl, $(CH_2)_m$heteroaryl, $CH(phenyl)_2$, $CH(C_{1-6}alkyl)(phenyl)$, $C_{2-4}$alkenyl(phenyl), $(CH_2)_pNR^cR^d$, $(CH_2)_pCONR^cR^d$, $(CH_2)_mCOR^c$ or $(CH_2)_m$ $CO_2R^c$ wherein said phenyl or heteroaryl group is optionally substituted by one or two substituents selected from halogen, $C_{1-6}$alkyl, $C_{1-6}$alkoxy, fluoro$C_{1-6}$alkyl, fluoro$C_{1-6}$alkoxy, $NO_2$, cyano, $SR^a$ or —$O(CH_2)_{1-2}O$—.

A particularly preferred group of compounds within this subclass is that wherein $R^7$represents $C_{3-6}$alkyl (especially propyl, isopropyl or isopentyl), $C_{5-7}$cycloalkyl (especially cyclohexyl), $C_{3-7}$cycloalkyl$C_{1-2}$alkyl (especially cyclopropylmethyl, cyclohexylmethyl or 2-cyclohexylethyl), $C_{2-4}$alkenyl (especially vinyl), naphthyl (especially 1-naphthyl), fluorenyl (especially 9-fluorenyl), $(CH_2)_m$phenyl (especially wherein m is 0, 1 or 2), $(CH_2)_m$ heteroaryl (especially wherein m is 0 or 1), $CH(phenyl)_2$, $CH(C_{1-2}alkyl)(phenyl)$, $C_{2-4}$alkenyl(phenyl) (especially $CH_2$—$CH$=$CH$ phenyl), $(CH_2)_pNR^cR^d$ (especially where $R^c$ and $R^d$ each represent $C_{2-4}$alkenyl; and especially wherein p is 2), $(CH_2)_pCONR^cR^d$ (especially wherein $R^c$ and $R^d$ each independently represent hydrogen, $C_{1-4}$alkyl, $C_{2-4}$alkenyl, phenyl or benzyl or $R^c$ and $R^d$, together with the nitrogen atom to which they are attached, form a heteroaliphatic ring of 5 or 6 atoms to which ring there is fused a benzene ring; and especially wherein p is 1), $(CH_2)_mCOR^c$ (especially wherein $R^c$ represents phenyl; and especially wherein m is zero) or $(CH_2)_mCO_2R^c$ (especially wherein $R^c$ represents hydrogen or $C_{1-4}$alkyl; and especially wherein m is zero or 1), wherein said phenyl or heteroaryl groups may be substituted by one or two groups independently selected from halogen, $C_{1-4}$alkyl, $C_{1-4}$alkoxy, fluoro$C_{1-4}$alkyl, fluoro$C_{1-4}$alkoxy, $NO_2$, cyano and $SR^a$ (especially wherein $R^a$ represents $C_{1-4}$alkyl), or said phenyl or heteroaryl group may be substituted by the group —$O(CH_2)_{1-2}O$—. Particularly preferred are compounds in which said phenyl groups are unsubstituted or substituted by one or two substituents independently selected from fluorine, chlorine, methyl, ethyl, methoxy, ethoxy, isopropoxy, trifluoromethoxy, nitro, cyano and thiomethyl, or said phenyl is substituted by —$OCH_2O$—. Also preferred are compounds in which said heteroaryl groups are unsubstituted or are monosubstituted by methyl or trifluoromethyl.

$R^7$ very aptly represents 2-methoxyphenyl.

Another preferred group of compounds of formula (I) is that wherein X represents an oxygen atom, two hydrogen atoms, or =NH. Most especially preferred are compounds wherein X is an oxygen atom.

A further preferred group of compounds of formula (I) is that wherein Y is —$CH_2CH_2$—, —$CH_2CH(CH_3)$—, —CH=CH— or —C≡C—, and most especially —$CH_2CH_2$—.

Another preferred group of compounds of formula (I) is that wherein X is two hydrogen atoms and Y is —$CH_2CH_2$—, —$CH_2C(O)$—, —$CH_2CHOH$— or —$CH_2CHF$—.

As used herein, $NR^cR^d$ is preferably $NH_2$, $NHCH_3$ or $N(CH_3)_2$; $NR^aCOR^b$ is preferably $NHCOCH_3$, $N(CH_3)COCH_3$ or $N(Ph)COCH_3$; $NR^aCO_2R^b$ is preferably $NHCO_2CH_3$ or $N(CH_3)CO_2CH_3$; $NR^aSO_2R^b$ is preferably $NHSO_2CH_3$, $N(CH_3)SO_2CH_3$ or $N(Ph)SO_2CH_3$; and $CO_2R^a$ is preferably $CO_2H$, $CO_2CH_3$ or $CO_2CH_2CH_3$.

When any variable occurs more than one time in formula (I) or in any substituent, its definition on each occurrence is independent of its definition at every other occurrence.

As used herein, the term "alkyl" or "alkoxy" as a group or part of a group encompasses both straight and branched embodiments. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and fluoro$C_{1-6}$alkoxy means a $C_{1-6}$alkyl or $C_{1-6}$alkoxy group in which one or more (in particular, 1 to 3) hydrogen atoms have been replaced by fluorine atoms. Similarly, the term "fluoro$C_{1-4}$alkyl" means a $C_{1-4}$alkyl group in which one or more (in particular 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "heteroaryl" as a group or part of a group means a heteroaromatic ring selected from pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzofuranyl, benzthiophenyl, benzimidazolyl, benzisoxazolyl, benzoxazolyl, benzthiazolyl or benzisothiazolyl. Particularly preferred examples of "heteroaryl" groups include pyridyl, indolyl and triazolyl, especially 2-pyridyl, 3-pyridyl, 2-indolyl and 1,2,4-triazol-3-yl.

When used herein the term "halogen" means fluorine, chlorine, bromine and iodine. The most apt halogens are fluorine and chlorine of which fluorine is preferred, unless otherwise stated.

A particularly preferred subset of the compounds of formula (I) are in accordance with formula (Ia):

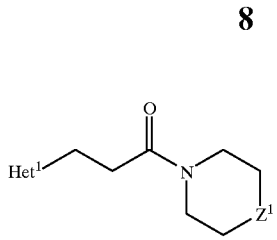
(Ia)

wherein $Het^1$ represents a residue selected from:

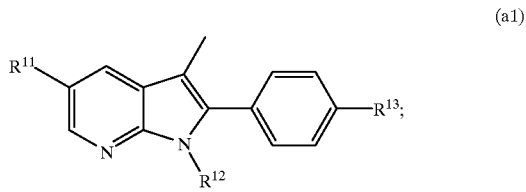
(a1)

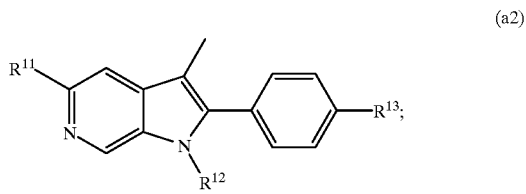
(a2)

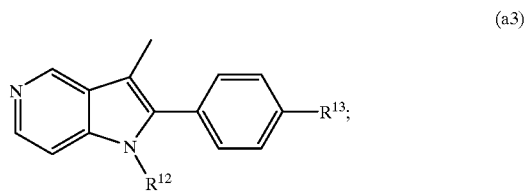
(a3)

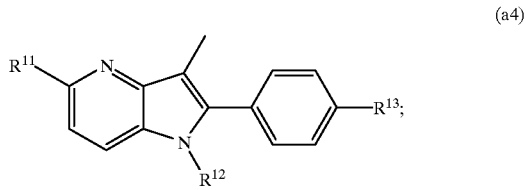
(a4)

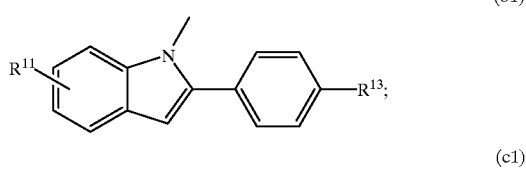
(b1)

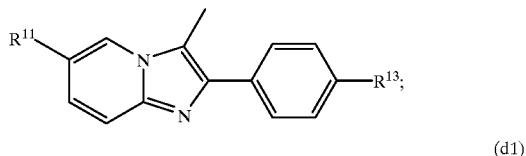
(c1)

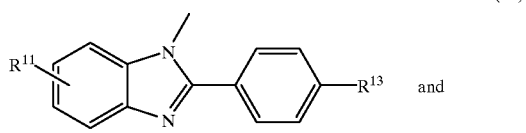
(d1)

and

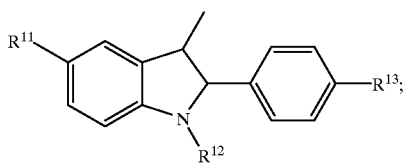
(e1)

$Z^1$ represents $CR^{15}R^{16}$ or $NR^{17}$;

$R^{11}$ represents hydrogen, chlorine or methyl, and when Het$^1$ represents (b1) or (d1), $R^{11}$ is in the 5-position or the 6-position;

$R^{12}$ represents a hydrogen atom or a group selected from $C_{1-3}$alkyl, fluoro$C_{1-3}$alkyl, $COCH_3$, or $(CH_2)_2OH$;

$R^{13}$ represents a halogen atom or a group selected from $C_{1-4}$alkyl, $C_{2-4}$alkenyl, fluoro$C_{1-4}$alkyl, $C_{1-4}$alkoxy or fluoro$C_{1-4}$alkoxy;

$R^{15}$ represents cyclohexyl, phenyl, 2-indolyl, $CH_2$phenyl, $CH_2CH_2$phenyl, CO(p-methoxyphenyl), $C(OH)(phenyl)_2$, $NR^cR^d$ or $CH_2NR^cR^d$ (where $R^c$ and $R^d$ each independently represent hydrogen, methyl, $COCH_3$, $COCH_2CH_3$, $SO_2CH_3$ or phenyl, or $R^c$ and $R^d$, together with the nitrogen atom to which they are attached, form a piperidine ring) and wherein each phenyl group is optionally substituted by one or two substituents selected from fluorine, chlorine, bromine, methyl, methoxy, trifluoromethoxy or $SO_2CH_3$;

$R^{16}$ represents hydrogen, fluorine, cyano, $NR^cR^d$ (where $R^c$ and $R^d$ each independently represent hydrogen or methyl), $NHCOCH_3$, $CH_2NHCOCH_3$, $CO_2H$, $CO_2CH_3$, OH or $CH_2OH$;

or $R^{15}$ and $R^{16}$ together are so linked as to form a 5- or 6-membered ring optionally substituted by =O, and optionally containing a double bond, which ring optionally contains in the ring an oxygen or sulfur atom or 1 or 2 NH groups, and to which ring is either fused or attached a benzene ring, which benzene ring is optionally substituted by methyl or $SO_2CH_3$;

$R^{17}$ represents a group selected from $C_{3-6}$alkyl, $C_{5-7}$cycloalkyl, $C_{3-7}$cycloalkyl$C_{1-2}$alkyl, phenyl, naphthyl, benzyl, α-methylbenzyl, phenylethyl, —$CH_2CON(CH_3)$ phenyl, —$CH_2CON(CH_3)$benzyl, —$CH_2CONR^cR^d$ (where $R^c$ and $R^d$, together with the nitrogen atom to which they are attached, form a heteroaliphatic ring of 5 or 6 atoms to which ring there is fused a benzene ring), —$CH_2CON(CH_3)C_{2-4}$alkenyl, or —$(CH_2)_mCO_2R^c$ (where $R^c$ is hydrogen or $C_{1-4}$alkyl and m is zero or 1), wherein said phenyl and benzyl groups may be substituted by a group selected from halogen, $C_{1-3}$alkyl, $C_{1-3}$alkoxy, fluoro$C_{1-3}$alkyl, fluoro$C_{1-3}$alkoxy, $NO_2$, cyano, and —S—$C_{1-3}$alkyl or said phenyl and benzyl groups may be substituted by the group —O—$CH_2$—O—.

Particularly preferred compounds of formula (Ia) are those wherein $R^{12}$ represents hydrogen, methyl, $COCH_3$ or —$(CH_2)_2OH$, especially hydrogen or methyl.

Another preferred class of compounds of formula (Ia) is that wherein $R^{13}$ represents chlorine, bromine, fluorine, methyl, ethyl, isopropyl, trifluoromethyl or vinyl, especially chlorine, bromine, fluorine or methyl A further preferred class of compounds of formula (Ia) is that wherein $Z^1$ represents $CR^{15}R^{16}$; $R^{15}$ represents cyclohexyl, phenyl, benzyl, 4-chlorophenyl, 3-trifluoromethylphenyl, NH(phenyl), N(CH$_3$)(phenyl) or N(COCH$_2$CH$_3$)(phenyl); and $R^{16}$ represents hydrogen, fluorine, hydroxy or $CO_2CH_3$. Very aptly, $R^{15}$ represents benzyl and $R^{16}$ represents hydroxy.

A further preferred class of compounds of formula (Ia) is that wherein $Z^1$ represents $NR^{17}$ and $R^{17}$ represents phenyl, benzyl, cyclohexyl, cyclohexylmethyl, cyclopropylmethyl, isopentyl, —$CH_2CON(CH_3)$phenyl, —$CH_2CON(CH_3)$ benzyl, or —$CH_2CO_2CH_2CH_3$, wherein said phenyl and benzyl groups may be substituted by a group selected from fluorine, chlorine, methyl, methoxy, trifluoromethoxy, $NO_2$, methylthio or by the group —O—$CH_2$—O—. Very aptly, $R^{17}$ represents 2-methoxyphenyl.

Examples of compounds in accordance with the invention include the following:

1-{3-[5-chloro-2-(4-chlorophenyl)-1-methyl-1H-pyrrolo[2,3-b]pyridine-3-yl]-1-oxopropyl}-4-(phenylmethyl)-4-piperidinol;

1-{3-[5-chloro-2-(4-chlorophenyl)-1-methyl-1H-pyrrolo[2,3-c]pyridine-3-yl]-1-oxopropyl}-4-(phenylmethyl)-4-piperidinol;

1-{3-[2-(4-chlorophenyl)-1-methyl-1H-pyrrolo[3,2-c]pyridine-3-yl]-1-oxopropyl}-4-(phenylmethyl)-4-piperidinol;

1-{3-[5-chloro-2-(4-chlorophenyl)-1-methyl-1H-pyrrolo[3,2-b]pyridine-3-yl]-1-oxopropyl}-4-(phenylmethyl)-4-piperidinol;

1-{3-[6-chloro-2-(4-chlorophenyl)imidazo[1,2-a]pyridine-3-yl]-1-oxopropyl}-4-(phenylmethyl)-4-piperidinol;

1-{3-[6-methyl-2-(4-methylphenyl)imidazo[1,2-a]pyridine-3-yl]-1-oxopropyl}-4-(2-methoxyphenyl)piperazine;

1-{3-[6-chloro-2-(4-fluorophenyl)-1-H-indol-1-yl]-1-oxopropyl}-4-(2-methoxyphenyl)piperazine;

1-{3-[5-chloro-2-(4-chlorophenyl)-1-H-indol-1-yl]-1-oxopropyl}-4-(2-methoxyphenyl)piperazine;

1-{3-[5-methyl-2-(4-methylphenyl)-1-H-benzimidazol-1-yl]-1-oxopropyl}-4-(2-methoxyphenyl)piperazine;

1-{3-[6-methyl-2-(4-methylphenyl)-1-H-benzimidazol-1-yl]-1-oxopropyl}-4-(2-methoxyphenyl)piperazine;

(2RS-cis)-1-{3-[5-chloro-2-(4-chlorophenyl)-2,3-dihydro-1-methyl-1-H-indol-3-yl]-1-oxopropyl}-4-(phenylmethyl)-4-piperidinol;

(2RS-trans)-1-{3-[5-chloro-2-(4-chlorophenyl)-2,3-dihydro-1-methyl-1H-indol-3-yl]-1-oxopropyl}-4-(phenylmethyl)-4-piperidinol;

(2RS-cis)-1-{3-[5-chloro-2-(4-chlorophenyl)-2,3-dihydro-1-methyl-1H-indol-3-yl]-1-oxopropyl}-4-(2-methoxyphenyl)piperazine; and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the compounds of formula (I) and salts thereof, for example, hydrates.

The compounds according to the invention may have at least one asymmetric centre, and may exist both as enantiomers and as diastereoisomers. It is to be understood that all such isomers and mixtures thereof are encompassed within the scope of the present invention.

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, wafers, powders, granules, solutions or suspensions, or suppositories, for oral, parenteral or rectal administration, or administration by inhalation or insufflation. Oral compositions such as tablets, pills, capsules or wafers, are particularly preferred.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, bronchospasm and cough; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a $5\text{-}HT_3$ antagonist, such as ondansetron, granisetron or tropisetron, or other anti-emetic medicaments, for example, a dopamine antagonist such as metoclopramide or domperidone or $GABA_B$ receptor agonists such as baclofen. Additionally, a compound of formula (I), either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929, 768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

Suitable methods for determining the anti-emetic effects of compounds of the present invention are well known in the art, for example, using the ferret model of cisplatin-induced emesis described by F. D. Tattersall et al, in *Eur. J. Pharmacol.*, (1993) 250, R5–R6.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache, including migraine, acute or chronic tension headache, cluster headache, temporomandibular pain, and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or depression.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination.

Thus, for example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, (α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and $5\text{-}HT_{1A}$ agonists or antagonists, especially $5\text{-}HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable $5\text{-}HT_{1A}$ receptor agonists or antagonists include, in particular, the $5\text{-}HT_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders, including obesity, bulimia nervosa and compulsive eating disorders.

The present invention also provides a method for the treatment or prevention of eating disorders, including obesity, bulimia nervosa and compulsive eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief.

In a further aspect of the present invention, there is provided a pharmaceutical composition for the treatment or prevention of obesity comprising a compound of formula (I) and an SSRI, together with at least one pharmaceutically acceptable carrier or excipient.

It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of formula (I) and an SSRI as a combined preparation for simultaneous, separate or sequential use in the treatment or prevention of obesity.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared ($kg/m^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycycstic ovarian disease, cardiovascular diseases, osteoarthritis, dermatological disorders, hypertension, insulin resistance, hypercholesterolemia, hypertriglyceridemia, and cholelithiasis.

A further aspect of the present invention comprises the use of a compound of formula (I) for achieving a chrono-biologic (circadian rhythm phase-shifting) effect and alleviating circadian rhythm disorders in a mammal. The present invention is further directed to the use of a compound of formula (I) for blocking the phase-shifting effects of light in a mammal.

The present invention further relates to the use of a compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of formula (I) or a pharmaceutically acceptable salt thereof.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

Compounds of formula (I) wherein X=O may be prepared by coupling of a carboxylic acid 1 with a cyclic amine 2:

1

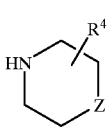

2 where Het, Y, Z and $R^4$ have the same meanings as before. The coupling may be effected using any of the coupling agents commonly used for promoting amide bond formation, such as carbonyldiimidazole (CDI) or 1-(3-dimethylaminopropyl)-3-ethylcarbodiimide hydrochloride (EDC) in combination with 1-hydroxybenzotriazole hydrate (HOBT). The reaction generally takes place at ambient temperature in an aprotic solvent in the presence of base.

Compounds of formula (I) wherein X=S may be prepared by treatment of the corresponding compounds wherein X=O with Lawesson's reagent. Likewise, compounds of formula (I) wherein X=two hydrogens may be obtained by reduction of the corresponding compounds wherein X=O, e.g. using borane/tetrahydrofuran complex. Alternatively, the compounds of formula (I) wherein X=two hydrogens may be obtained by reductive alkylation of the amines 2 by the aldehydes 3:

3 where Het and Y have the same meanings as before. The reaction is conveniently effected in dichloroethane solution in the presence of sodium triacetoxyborohydride and glacial acetic acid. The aldehydes 3 are obtainable by reduction of the alkyl esters of the carboxylic acids 1, e.g. using diisobutylaluminium hydride in an inert solvent.

When Het represents heterocyclic residue (a), the acids 1 may be obtained by reaction of the iodopyridinamines 4 with the alkynes 5, followed by hydrolysis of the methyl ester group:

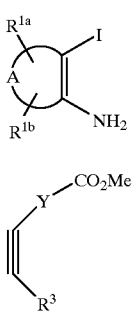

4

5 where A, $R^{1a}$, $R^{1b}$, Y and $R^3$ have the same meanings as before. The reaction may be carried out at 100° C. in DMF in the presence of palladium (II) acetate, triphenylphosphine, lithium chloride and sodium carbonate.

When Het represents heterocyclic residue (b) in which the optional double bond indicated by the dotted line is present, the acids 1 may be obtained by alkylation of the indole derivatives 6 with the esters 7, followed by hydrolysis of the ester group:

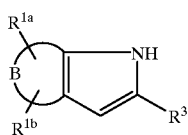

6

Hal—Y—CO$_2$R  7 where Hal represents a leaving group such as halogen, especially chlorine or bromine, R represents an alkyl group, such as methyl or ethyl, and B, $R^{1a}$, $R^{1b}$, Y and $R^3$ have the same meanings as before. Alternatively, the indoles 6 may undergo Michael addition to methyl or ethyl acrylate, followed by hydrolysis of the ester function, to provide acids 1 in which Y represents —CH$_2$CH$_2$—. The addition reaction may be carried out at moderately elevated temperatures in the presence of a base such as potassium carbonate.

The indoles 6 may be prepared by coupling of an iodoamine 8 with an alkyne $R^3$—C≡CH to form the adduct 9, which is subsequently cyclised to 6:

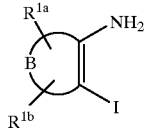

8

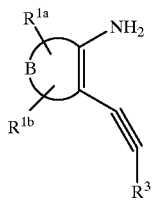

9 where B, $R^{1a}$, $R^{1b}$ and $R^3$ have the same meanings as before. The coupling takes place in the presence of a Pd(0) catalyst, cuprous iodide and diethylamine, and the cyclisation of 9 may be effected by heating at 120° C. in DMF solution in the presence of calcium carbonate and cuprous iodide.

Alternatively, an amine 10 may be reacted with $R^3$—COCl to form the amide 11, which is subsequently cyclised to 6:

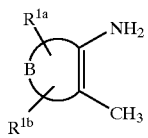

10

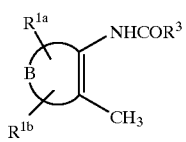

11 where B, $R^{1a}$, $R^{1b}$ and $R^3$ have the same meanings as before. The cyclisation of 11 to 6 may be effected by treatment with butyllithium in THF.

When Het represents heterocyclic residue (c), the acids 1 may be prepared from the aldehydes 12 which are in turn available from the azaindoles 13 by reaction with N-(chloromethylene)-N-methylmethanaminium chloride:

12

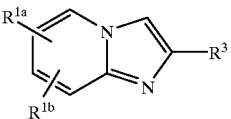

13 where $R^{1a}$, $R^{1b}$ and $R^3$ have the same meanings as before. The azaindoles 13 may be prepared by reaction of the appropriate 2-aminopyridines with $R^3$—COCH$_2$Br in the presence of base. Reaction of aldehydes 12 with ethyl (diethoxyphosphinyl)acetate, or with a suitable Wittig reagent, in the presence of strong base provides the ethyl esters of the acids 1 in which Het represents (c) and Y represents —CH=CH—.

When Het represents heterocyclic residue (d), the acids 1 may be prepared from the imidazoles 14 by N-alkylation with 7 or Michael addition to methyl or ethyl acrylate, by the methods described previously for the indoles 6. The imidazoles 14 are available by reaction of the diamines 15 with $R^3$—COCl:

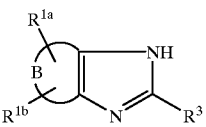

14

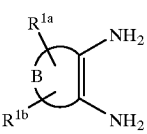

15 where B, $R^{1a}$, $R^{1b}$ and $R^3$ have the same meanings as before. The first step of the reaction is carried out at ambient temperature or below in a solvent such as dichloromethane in the presence of a tertiary amine, and then the initially-formed anilide is heated with acetic acid at about 100° C. to effect cyclisation to 14.

When Het represents heterocyclic residue (e), the acids 1 may be prepared by reduction of the indole derivatives 16:

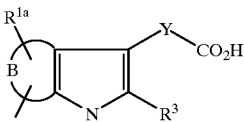

16 where B, Y, $R^{1a}$, $R^{1b}$ and $R^3$ have the same meanings as before. The reduction may be effected by any of the conventional methods, e.g. by treatment with sodium cyanoborohydride in trifluoroacetic acid. In an alternative (and preferred) synthesis sequence, the reduction of the indole ring is carried out subsequent to the coupling of acid 16 with amine 2. The indoles 16 are available by reaction of arylhydrazines 17 with ketones 18:

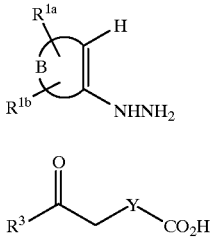

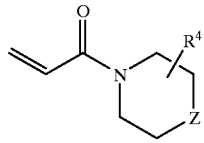

where B, Y, $R^{1a}$, $R^{1b}$ and $R^3$ have the same meanings as before. The reagents are allowed to react at ambient temperature in ethanol to form an adduct which is subsequently refluxed in trifluoroacetic acid to complete the cyclisation.

In an alternative route to the compounds of formula (I) wherein Y represents —CH$_2$CH$_2$—, X is O, and Het represents heterocyclic residues (b) or (d), indoles 6 or imidazoles 14 are reacted with propenamides 19:

19 where Z and $R^4$ have the same meanings as before. The addition reaction may be carried out in DMF solution at about 100° C. in the presence of a base such as potassium carbonate.

Where they are not commercially available, the starting materials 2, 4, 5, 7, 8, 10, 15, 17, 18, 19, $R^3$—C≡CH, $R^3$COCl and $R^3$COCH$_2$Br may be prepared by the methods described in the worked examples provided herein, or by other standard methods known to those skilled in the art.

It will be appreciated that a particular compound in accordance with formula (I) may be converted to a different compound, also in accordance with formula (I), by standard synthetic procedures. For example, compounds of formula (I) in which Het represents (a) or (e) and $R^2$ is H may be converted to the corresponding compounds in which $R^2$ is other than H by conventional methods of N-alkylation or acylation. (Alternatively, such procedures can be carried out on the synthetic precursors of the relevant compounds of formula (I)).

Similarly, a compound of formula (I) wherein Het represents (b) and the optional double bond represented by the dotted line is present may be reduced to the corresponding 2,3-dihydroindole (in which the aforesaid double bond is absent) by standard methods, such as treatment with sodium cyanoborohydride in trifluoroacetic acid.

As a further example of this protocol, compounds of formula (I) in which Y represents a linear alkylene chain may be alkylated at the carbon atom of Y adjacent to the carbonyl group, thereby providing the corresponding compounds of formula (I) wherein Y represents a branched alkylene chain. Any of the normal techniques of C-alkylation may be used, such as treatment with sodium hydride and the appropriate alkyl halide.

Similarly, compounds of formula (I) wherein Y represents —CH═CH— may be converted to the corresponding compounds in which Y represents —CH$_2$CH$_2$—. The reduction may be effected by any of the standard techniques, such as treatment with sodium borohydride in pyridine solution.

The compounds of formula (I) prepared according to the methods described above may be isolated and purified in a conventional manner, for example, extraction, precipitation, fractional crystallization, recrystallization, chromatography or a combination thereof.

Although the reaction schemes described herein are reasonably general, it will be understood by those skilled in the art of organic synthesis that one or more functional groups present in a given compound of formula (I) may render the molecule incompatible with a particular synthetic sequence. In such a case an alternative route, an altered order of steps, or a strategy of protection and deprotection may be employed. In all cases the particular reaction conditions, including reagents, solvent, temperature, and time, should be chosen so that they are consistent with the nature of the functionality present in the molecule.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with IC$_{50}$ at the NK$_1$ receptor of less than 100 nM on said test method.

The following non-limiting Examples serve to illustrate the preparation of compounds of the present invention:

EXAMPLES

Description 1

Methyl 4-pentynoate

Acetyl chloride (22.0 mL, 24.3 g, 0.31 mol) was added dropwise over 15 min. to a solution of 4-pentynoic acid (20 g, 204 mmol) in methanol (100 mL) and the mixture was heated under reflux for 4 h. The mixture was cooled, poured into aqueous sodium hydroxide (1M) and extracted with ether. The combined organic fractions were washed with aqueous sodium hydroxide (1M), dried (MgSO$_4$) and the solvent was evaporated under reduced pressure to give the title compound as a pale yellow oil (22.5 g, 98%). $^1$H NMR (360 MHz, CDCl$_3$) δ 3.70 (3H, s), 2.24 (4H, m), and 1.98 (1H, t, J 2.7 Hz).

Description 2

Methyl 5-(4-Chlorophenyl)-4-pentynoate

A mixture of 1-chloro-4-iodobenzene (56 g, 235 mmol), dichlorobis(triphenylphosphine)palladium (II) (6.9 g, 9.8 mmol) and copper (I) iodide (1.9 g, 9.8 mmol) in diethylamine (200 mL) was degassed with bubbling nitrogen. Methyl 4-pentynoate (Description 1, 22.0 g, 196 mmol) was added dropwise and the mixture was degassed with bubbling nitrogen. The mixture was heated under reflux for 24 h., cooled and poured into saturated aqueous ammonium chloride. The mixture was extracted with ethyl acetate and the combined organic fractions were washed with saturated aqueous ammonium chloride. The solvent was evaporated under reduced pressure and the residue was triturated with hexane. The mixture was filtered, dried (MgSO$_4$) and concentrated under reduced pressure. The mixture was refrigerated and the solid was collected and dried in vacuo to give the title compound as pale brown solid (21.0 g, 48%). $^1$H NMR (360 MHz, CDCl$_3$) δ 7.31 (2H, d, J 7.5 Hz), 7.25 (2H, d, J 7.5 Hz), 3.72 (3H, s), 2.73 (2H, t, J 7.3 Hz), and 2.62 (2H, t, J 7.3 Hz).

Description 3

5-Chloro-3-iodo-2-pyridinamine

Iodine (13.2 g, 52 mmol) was added to a mixture of 5-chloro-2-pyridinamine (6.68 g, 52 mmol) and silver sulfate (16.2 g, 52 mmol) in ethanol (350 mL) and the mixture was stirred at room temperature for 20 h. The mixture was filtered through a glass fibre pad and the solvent was evaporated under reduced pressure. The residue was dissolved in dichloromethane (600 mL), washed with aqueous sodium hydroxide (5%, 500 mL), water (500 mL) and brine (500 mL), dried (Na$_2$SO$_4$) and the solvent was evaporated under reduced pressure. The residue was purified by flash column chromatography on silica gel, eluting with isohexane/EtOAc (80:20), to give the title compound as a pale orange solid (7.1 g, 54%). $^1$H NMR (360 MHz, CDCl$_3$) δ 7.99 (1H, d, J 2.2 Hz), 7.84 (1H, d, J 2.2 Hz), and 4.94 (2H, br s). m/z (ES$^+$) 255, 257 (M+1).

Description 4

Methyl 5-Chloro-2-(4-chlorophenyl)-1H-pyrrolo[2,3-b]pyridine-3-propanoate

A mixture of 5-chloro-3-iodo-2-pyridinamine (Description 3, 2.31 g, 9.1 mmol), methyl 5-(4-chlorophenyl)-4-pentynoate (Description 2, 3.03 g, 13.6 mmol), triphenylphosphine (126 mg, 0.48 mmol), lithium chloride (385 mg, 9.1 mmol) and sodium carbonate (4.82, 45.5 mmol) in dimethylformamide (75 mL) was degassed with bubbling nitrogen, then palladium (II) acetate (102 mg, 0.45 mmol) was added and the mixture was stirred at 100° C. for 18 h. The mixture was cooled and further triphenylphosphine (126 mg, 0.48 mmol) and palladium (II) acetate (102 mg, 0.45 mmol) were added. The mixture was degassed with bubbling nitrogen and stirred at 100° C. for 6 h. The mixture was poured into saturated aqueous ammonium chloride and water and extracted with ethyl acetate. The combined organic fractions were washed with water and brine, dried (MgSO$_4$) and the solvent was evaporated under reduced pressure. The residue was purified by flash column chromatography on silica gel, eluting with isohexane/EtOAc (90:10 increasing to 75:25), to give the title compound (530 mg, 17%). $^1$H NMR (360 MHz, CDCl$_3$) δ 10.90 (1H, br s), 8.10 (1H, d, J 2.2 Hz), 7.92 (1H, d, J 2.2 Hz), 7.60–7.52 (4H, m), 3.64 (3H, s), 3.19 (2H, t, J 7.9 Hz), and 2.65 (2H, t, J 7.9 Hz).

Description 5

Methyl 5-Chloro-2-(4-chlorophenyl)-1-methyl-1H-pyrrolo[2,3-b]pyridine-3-propanoate Sodium hydride (60% suspension in mineral oil, 15 mg, 0.38 mmol) was added to a stirred, cooled (0° C.) solution of methyl 5-chloro-2-(4-chlorophenyl)-1H-pyrrolo[2,3-b]pyridine-3-propanoate (Description 4, 82 mg, 0.23 mmol) in dimethylformamide (5 mL) and the mixture was stirred at room temperature for 10 min. Iodomethane (24 μL, 54 mg, 0.38 mmol) was added and the mixture was stirred at room temperature for 5 min. Water (15 mL) was added and the mixture was extracted with ethyl acetate (3×15 mL). The combined organic fractions were washed with brine, dried (MgSO$_4$) and the solvent was evaporated under reduced pressure to give the title compound (82 mg, 96%). $^1$H NMR (360 MHz, CDCl$_3$) δ 8.27 (1H, d, J 2.2 Hz), 7.87 (1H, d, J 2.2 Hz), 7.50 (2H, m), 7.34 (2H, m), 3.64 (3H, s), 3.60 (3H, s), 2.98 (2H, t, J 7.8 Hz), and 2.51 (2H, t, J 7.8 Hz).

Description 6

1,1-Dimethylethyl (6-Chloro-3-pyridinyl)carbamate

Di-t-butyldicarbonate (9.3 g, 43 mmol) was added to a solution of 6-chloro-3-pyridinamine (4.58 g, 35.6 mmol) in 1,4-dioxane (50 mL) and the mixture was heated under reflux for 18 h. The mixture was cooled and poured into water. The mixture was extracted with ether and the combined organic fractions were washed with water, dried (MgSO$_4$) and the solvent was evaporated under reduced pressure. The residue was triturated with hexane and the solid was collected and dried in vacuo to give the title compound as an off-white solid (7.68 g, 94%). $^1$H NMR (400 MHz, CDCl$_3$) δ 8.23 (1H, s), 7.96 (1H, br d, J 7.2 Hz), 7.25 (1H, d, J 7.2 Hz), 6.54 (1H, br s), and 1.52 (9H, s). m/z (ES$^+$) 229, 231 (M+1).

Description 7

1,1-Dimethylethyl (6-Chloro-4-iodo-3-pyridinyl)carbamate n-Butyllithium (1.6M in hexanes, 22 mL, 35 mmol) was added dropwise to a stirred, cooled (−78° C.) solution of 1,1-dimethylethyl (6-chloro-3-pyridinyl)carbamate (Description 6, 2.68 g, 11.7 mmol) and N,N,N',N'-tetramethylethylenediamine (5.3 mL, 4.1 g, 35 mmol) in ether (60 mL). The mixture was allowed to warm to −10° C. and stirred for 2 h. The mixture was cooled to −78° C. and a cooled (−10° C.) solution of iodine (6.0 g, 24 mmol) in ether (20 mL) was added dropwise. The mixture was allowed to warm to room temperature and stirred for 18 h. Saturated aqueous ammonium chloride was added and the mixture was extracted with ether. The combined organic fractions were washed with aqueous sodium metabisulfite (10%), dried (MgSO$_4$) and the solvent was evaporated under reduced pressure. The residue was triturated with hexane and the solid was collected and dried in vacuo to give the title compound as a brown solid (2.3 g, 55%). $^1$H NMR (400 MHz, CDCl$_3$) δ 8.94 (1H, s), 7.73 (1H, s), 6.64 (1H, br s), and 1.54 (9H, s).

Description 8

6-Chloro-4-iodo-3-pyridinamine

Trifluoroacetic acid (2.4 mL) was added to a solution of 1,1-dimethylethyl (6-chloro-4-iodo-3-pyridinyl)carbamate (Description 7, 2.2 g, 6.2 mmol) in dichloromethane (50 mL) and the mixture was stirred at room temperature for 24 h. The solvent was evaporated under reduced pressure and the residue was dissolved in ethyl acetate. The mixture was washed with aqueous sodium hydroxide (1M), dried (MgSO$_4$) and the solvent was evaporated under reduced pressure. The residue was purified by flash column chromatography on silica gel, eluting with isohexane/EtOAc (70:30), to give the title compound as a yellow solid (1.3 g, 82%). $^1$H NMR (360 MHz, CDCl$_3$) δ 7.80 (1H, s), 7.60 (1H, s), and 4.13 (2H, br s). m/z (ES$^+$) 255, 257 (M+1).

Description 9

Methyl 5-Chloro-2-(4-chlorophenyl)-1H-pyrrolo[2,3-c]pyridine-3-propanoate

Prepared from 6-chloro-4-iodo-3-pyridinamine (Description 8) and methyl 5-(4-chlorophenyl)-4-pentynoate (Description 2) according to the method of Description 4. $^1$H NMR (360 MHz, CDCl$_3$) δ 8.56 (1H, br s), 8.50 (1H, s), 7.50 (5H, m), 3.63 (3H, s), 3.15 (2H, t, J 7.9 Hz), and 2.62 (2H, t, J 7.9 Hz). m/z (ES$^+$) 349, 351 (M+1).

Description 10

Methyl 5-Chloro-2-(4-chlorophenyl)-1-methyl-1-H-pyrrolo[2,3-c]pyridine-3-propanoate Prepared from methyl 5-chloro-2-(4-chlorophenyl)-1H-pyrrolo[2,3-c]pyridine-3-propanoate (Description 9) according to the method of Description 5. $^1$H NMR (360 MHz, CDCl$_3$) δ 8.49 (1H, s), 7.52 (3H, m), 7.32 (2H, d, J 8.6 Hz), 3.62 (3H, s), 3.60 (3H, s), 2.95 (2H, t, J 7.8 Hz), and 2.50 (2H, t, J 7.8 Hz).

Description 11

3-Iodo-4-pyridinamine

Prepared from 4-pyridinamine according to the method of Description 3. $^1$H NMR (250 MHz, CDCl$_3$) δ 8.56 (1H, s), 8.10 (1H, d, J 5.5 Hz), 6.60 (1H, d, J 5.5 Hz), and 4.75 (2H, br s).

Description 12

Methyl 2-(4-Chlorophenyl)-1-H-pyrrolo ]3,2-c] pyridine-3-propanoate

Prepared from 3-iodo-4-pyridinamine (Description 11) and methyl 5-(4-chlorophenyl)-4-pentynoate (Description 2) according to the method of Description 4. $^1$H NMR (360 MHz, CDCl$_3$) δ 8.95 (1H, s), 8.45 (1H, br s), 8.34 (1H, d, J 5.8 Hz), 7.45 (4H, m), 7.28 (1H, d, J 5.8 Hz), 3.63 (3H, s), 3.25 (2H, t, J 8.0 Hz), and 2.70 (2H, t, J 8.0 Hz). m/z (ES$^+$) 315, 317 (M+1).

Description 13

Methyl 2-(4-Chlorophenyl)-1-methyl-1H-pyrrolo[3,2-c]pyridine-3-propanoate

Prepared from methyl 2-(4-chlorophenyl)-1H-pyrrolo[3,2-c]pyridine-3-propanoate (Description 12) according to the method of Description 5. $^1$H NMR (360 MHz, CDCl$_3$) δ 8.92 (1H, br s), 8.37 (1H, br d, J 5.0 Hz), 7.51 (2H, d, J 8.4 Hz), 7.33 (2H, d, J 8.4 Hz), 7.23 (1H, br d, J 5.0 Hz), 3.60 (3H, s), 3.55 (3H, s), 3.05 (2H, t, J 7.9 Hz), and 2.59 (2H, t, J 7.9 Hz). m/z (ES$^+$) 315, 317 (M+1).

Description 14

6-Chloro-2-iodo-3-pyridinamine

Prepared from 6-chloro-3-pyridinamine according to the method of Description 3. $^1$H NMR (360 MHz, CDCl$_3$) δ 7.05 (1H, d, J 8.2 Hz), 6.89 (1H, d, J 8.2 Hz), and 4.12 (2H, br s). m/z (ES$^+$) 255, 257 (M+1).

Description 15

Methyl 5-Chloro-2-(4-chlorophenyl)-1H-pyrrolo[3,2-b]pyridine-3-propanoate

Prepared from 6-chloro-2-iodo-3-pyridinamine (Description 14) and methyl 5-(4-chlorophenyl)-4-pentynoate (Description 2) according to the method of Description 4. $^1$H NMR (500 MHz, CDCl$_3$) δ 8.20 (1H, br s), 7.56 (1H, d, J 8.4 Hz), 7.52 (2H, d, J 8.5 Hz), 7.47 (2H, d, J 8.5 Hz), 7.11 (1H, d, J 8.4 Hz), 3.61 (3H, s), 3.21 (2H, t, J 7.8 Hz), and 2.85 (2H, t, J 7.8 Hz).

Description 16

Methyl 5-Chloro-2-(4-chlorophenyl)-1-methyl-1-H-pyrrolo[3,2-b]pyridine-3-propanoate Prepared from methyl 5-chloro-2-(4-chlorophenyl)-1H-pyrrolo[3,2-b]pyridine-3-propanoate (Description 15) according to the method of Description 5. $^1$H NMR (360 MHz, CDCl$_3$) δ 7.54 (1H, d, J 8.5 Hz), 7.51 (2H, d, J 8.4 Hz), 7.35 (2H, d, J 8.4 Hz), 7.14 (1H, d, J 8.5 Hz), 3.59 (3H, s), 3.56 (3H, s), 3.05 (2H, t, J 7.8 Hz), and 2.76 (2H, t, J 7.8 Hz). m/z (ES$^+$) 363, 365 (M+1).

Description 17

6-Chloro-2-(4-chlorophenyl)imidazo[1,2-a]pyridine

2-Bromo-1-(4-chlorophenyl)ethanone (9.08 g, 39 mmol) was added to a solution of 5-chloro-2-pyridinamine (5.0 g, 39 mmol) in dimethylformamide (100 mL) and the mixture was heated under reflux for 20 h. The mixture was cooled and poured into water (400 mL) and the solid was collected. The solid was dissolved in dichloromethane (300 mL), washed with water (50 mL) and brine (50 mL), dried (MgSO$_4$) and the solvent was evaporated under reduced pressure. The residue was recrystallised from ethanol/water and the solid was collected and dried in vacuo to give the title compound (0.9 g, 9%). $^1$H NMR (360 MHz, CDCl$_3$) δ 8.17 (1H, d, J 2.0 Hz), 7.87 (2H, d, J 8.9 Hz), 7.81 (1H, s), 7.56 (1H, d, J 9.5 Hz), 7.41 (2H, d, J 8.9 Hz), and 7.16 (1H, dd, J 9.5, 2.0 Hz). n/z (ES$^+$) 263, 265 (M+1).

Description 18

6-Chloro-2-(4-chlorophenyl)imidazo[1,2-a]pyridine-3-carboxaldehyde

N-(Chloromethylene)-N-methylmethanaminium chloride (1.17 g, 9.1 mmol) was added to a solution of 6-chloro-2-(4-chlorophenyl)imidazo[1,2-a]pyridine (Description 17, 0.8 g, 3.0 mmol) in dimethylformamide (50 mL) and the mixture was stirred at 75° C. overnight. The mixture was cooled and poured onto a mixture of ice (500 g) and aqueous sodium hydroxide (2M, 500 mL). The solid was collected, dissolved in dichloromethane, washed with brine, dried (MgSO$_4$) and the solvent was evaporated under reduced pressure. The residue was triturated with ether and the solid was collected and dried in vacuo to give the title compound as a colorless solid (0.7 g, 79%). $^1$H NMR (360 MHz, CDCl$_3$) δ 10.06 (1H, s), 9.75 (1H, d, J 1.8 Hz), 7.77 (2H, d, J 8.5 Hz), 7.75 (1H, d, J 9.4 Hz), 7.53 (2H, d, J 8.5 Hz), and 7.56 (1H, dd, J 9.4, 1.8 Hz). m/z (ES$^+$) 291, 293 (M+1).

Description 19

(E)-Ethyl 3-[6-Chloro-2-(4-chlorophenyl)imidazo[1,2-a]pyridin-3-yl]-2-propenoate Ethyl (diethoxyphosphinyl)acetate (0.44 mL, 0.50 g, 2.2 mmol) was added dropwise to a suspension of sodium hydride (60% in mineral oil, 98 mg, 2.5 mmol) in 1,2-dimethoxyethane (10 mL) and the mixture was stirred at room temperature for 1 h. A suspension of 6-chloro-2-(4-chlorophenyl)imidazo[1,2-a]pyridine-3-carboxaldehyde (Description 18, 650 mg, 2.2 mmol) in 1,2-dimethoxyethane (10 mL) was added and the mixture was stirred at room temperature for 1 h. Further sodium hydride (60% in mineral oil, 98 mg, 2.5 mmol) was added and the mixture was stirred at room temperature for 2 h. Water (100 mL) was added and the solid was collected. Toluene was added and evaporated under reduced pressure and the residue was dried in vacuo to give the title compound as a pale brown solid (380 mg, 47%). $^1$H NMR (360 MHz, CDCl$_3$) δ 8.47 (1H, d, J 1.8 Hz), 7.94 (1H, d, J 16.4 Hz), 7.68 (3H, m), 7.48 (2H, d, J 8.4 Hz), 7.34 (1H, dd, J 9.4, 1.8 Hz), 6.37 (1H, d, J 16.4 Hz), 4.30 (2H, q, J 7.1 Hz), and 1.36 (3H, t, J 7.1 Hz).

Description 20

(E)-1-{3-[6-Chloro-2-(4-chlorophenyl)imidazo[1,2-a]pyridine-3-yl]-1-oxo-2-propenyl}-4-(phenylmethyl)-4-piperidinol Prepared from (E)-ethyl 3-[6-chloro-2-(4-chlorophenyl)-imidazo[1,2-a]pyridin-3-yl]-2-propenoate (Description 19) according to the method of Example 1. $^1$H NMR (360 MHz, CDCl$_3$) δ 8.36 (1H, d, J 1.5 Hz), 7.89 (1H, d, J 15.6 Hz), 7.71 (2H, d, J 8.5 Hz), 7.63 (1H, d, J 9.6 Hz), 7.44 (2H, d, J 8.5 Hz), 7.30 (4H, m), 7.19 (2H, d, J 7.3 Hz), 6.80 (1H, d, J 15.6 Hz), 4.49 (1H, m), 3.56 (1H, m), 3.43 (1H, m), 3.08 (1H, m), 2.78 (2H, s), and 1.65 (4H, m). m/z (ES$^+$) 506, 508 (M+1).

Description 21

6-Methyl-2-(4-methylphenyl)imidazo[1,2-a]pyridine

A solution of 2-bromo-1-(4-methylphenyl)ethanone (99.3 g, 0.47 mol) in dimethylformamide (250 mL) was added slowly to a solution of 5-methyl-2-pyridinamine (50.4 g, 0.47 mol) in dimethylformamide (250 mL). Sodium hydrogen carbonate (78.3 g, 0.93 mol) was added in portions and the mixture was stirred at room temperature for 15 min., then under reflux for 1.5 h. The mixture was cooled and poured into water (2500 mL). The solid was collected, washed with water (1000 mL) and recrystallised from dimethylformamide (400 mL). The solid was collected and dried in vacuo at 120° C. to give the title compound (89 g, 86%). $^1$H NMR (360 MHz, DMSO-d$_6$) δ 8.30 (1H, d, J 1.5 Hz), 8.23 (1H, s), 7.84 (2H, d, J 8.0 Hz), 7.47 (1H, d, J 9.2 Hz), 7.25 (2H, d, J 8.0 Hz), 7.09 (1H, dd, J 9.2, 1.5 Hz), 2.33 (3H, s), and 2.28 (3H, s).

Description 22

6-Methyl-2-(4-methylphenyl)imidazo[1,2-a]pyridine-3-carboxaldehyde

Prepared from 6-methyl-2-(4-methylphenyl)imidazo[1,2-a]pyridine (Description 21) according to the method of Description 18. $^1$H NMR (360 MHz, CDCl$_3$) δ 10.03 (1H, s), 9.48 (1H, d, J 1.6 Hz), 7.72 (2H, d, J 7.9 Hz), 7.70 (1H, d, J 8.8 Hz), 7.43 (1H, dd, J 8.8, 1.6 Hz), 7.33 (2H, d, J 7.9 Hz), and 2.44 (6H, s).

Description 23

(E)-Ethyl 3-[6-Methyl-2-(4-methylphenyl)imidazo[1,2-a]pyridin-3-yl]-2-propenoate Prepared from 6-methyl-2-(4-methylphenyl)imidazo[1,2-a]pyridine-3-carboxaldehyde (Description 22) according to the method of Description 19. $^1$H NMR (360 MHz, CDCl$_3$) δ 8.25 (1H, d, J 1.5 Hz), 8.04 (1H, d, J 16.3 Hz), 7.63 (3H, m), 7.30 (2H, d, J 8.0 Hz), 7.21 (1H, dd, J 9.1, 1.5 Hz), 6.35 (1H, d, J 16.3 Hz), 4.28 (2H, q, J 7.1 Hz), 2.43 (6H, s), and 1.34 (3H, t, J 7.1 Hz). m/z (ES$^+$) 321 (M+1).

Description 24

(E)-1-{3-[6-Methyl-2-(4-methylphenyl)imidazo[1,2-a]pyridine-3-yl]-1-oxo-2-propenyl}-4-(2-methoxyphenyl)piperazine Prepared from (E)-ethyl 3-[6-methyl-2-(4-methylphenyl)-imidazo[1,2-a]pyridin-3-yl]-2-propenoate (Description 23) and 1-(2-methoxyphenyl)piperazine according to the method of Example 1. $^1$H NMR (360 MHz, CDCl$_3$) δ 8.15 (1H, d, J 1.5 Hz), 8.01 (1H, d, J 15.5 Hz), 7.66 (2H, d, J 8.2 Hz), 7.59 (1H, d, J 9.1 Hz), 7.27 (2H, d, J 8.2 Hz), 7.15 (1H, dd, J 9.1, 1.5 Hz), 7.04 (1H, m), 6.92 (3H, m), 6.80 (1H, d, J 15.5 Hz), 3.91 (2H, br s), 3.89 (3H, s), 3.60 (2H, br s), 3.06 (4H, br s), and 2.40 (6H, s). m/z (ES$^+$) 467 (M+1).

Description 25

4-(2-Methoxyphenyl)-1-(1-oxo-2-propenyl)piperazine

Acryloyl chloride (10.6 mL, 11.8 g, 0.13 mol) was added dropwise to a stirred, cooled (0° C.) mixture of 1-(2-methoxyphenyl)piperazine hydrochloride (15 g, 66 mmol) and triethylamine (27.3 g, 19.8 g, 0.20 mol) in dichloromethane and the mixture was stirred at room temperature for 2 h. The mixture was poured into hydrochloric acid (1M) and extracted with dichloromethane. The combined organic fractions were washed with aqueous sodium hydrogen carbonate (saturated), dried (MgSO$_4$) and the solvent was evaporated under reduced pressure. The residue was purified by flash column chromatography on silica gel, eluting with isohexane/EtOAc (40:60 increasing to 20:80), to give the title compound as a pale yellow oil (3.6 g, 22%). $^1$H NMR (360 MHz, CDCl$_3$) δ 7.04 (1H, m), 6.95–6.84 (3H, m), 6.61 (1H, dd, J 16.8, 10.6 Hz), 6.32 (1H, dd, J 16.8, 1.8 Hz), 5.72 (1H, dd, J 10.6, 1.8 Hz), 3.94–3.84 (2H, m), 3.89 (3H, s), 3.74 (2H, m), and 3.06 (4H, m). m/z (ES$^+$) 247 (M+1).

Description 26

6-Chloro-2-(4-fluorophenyl)-1H-indole

A mixture of 5-chloro-2-iodoaniline (33.0 g, 0.13 mol) and 1-ethynyl-4-fluorobenzene (26.4 g, 0.22 mol) in diethylamine (400 mL) was degassed with bubbling nitrogen for 20 min., then tetrakis(triphenylphosphine)palladium(0) (2.0 g, 1.7 mmol) and copper (I) iodide (170 mg, 0.9 mmol) were added and the mixture was stirred at room temperature for 12 h. The solvent was evaporated under reduced pressure, water was added and the mixture was extracted with ethyl acetate. The combined organic fractions were washed with water (2×), dried (MgSO$_4$) and the solvent was evaporated under reduced pressure. The residue was dissolved in dimethylformamide (250 mL), calcium carbonate (13 g, 0.13 mol) and copper (I) iodide (12.4 g, 0.07 mol) were added and the mixture was stirred at 120° C. for 22 h. The mixture was cooled, filtered and the solvent was evaporated under reduced pressure. Water was added and the mixture was extracted with ethyl acetate. The combined organic fractions were washed with water (2×) and brine, dried (MgSO$_4$) and the solvent was evaporated under reduced pressure. The residue was triturated with ether/hexane and the solid was collected and dried in vacuo to give the title compound (25.4 g, 85%). $^1$H NMR (360 MHz, CDCl$_3$) δ 7.59 (2H, m), 7.49 (1H, d, J 8.5 Hz), 7.44 (1H, s), 7.24–6.99 (3H, m), and 6.69 (1H, d, J 1.8 Hz).

Description 27

4-Chloro-N-(4-chloro-2-methylphenyl)benzamide

4-Chlorobenzoyl chloride (19.5 g, 111 mmol) was added over 10 min. to a stirred, cooled (0° C.) solution of 4-chloro-2-methylaniline (15 g, 106 mmol) and triethylamine (22.2 mL, 16.1 g, 159 mmol) in dichloromethane (300 mL) and the mixture was stirred at room temperature for 2 h. Water (100 mL) was added and the dichloromethane was evaporated under reduced pressure. Aqueous sodium hydrogen carbonate (saturated, 200 mL), water (200 mL) and ethyl acetate (1000 mL) were added and the layers were separated. The organic layer was dried (MgSO$_4$) and the solvent was evaporated under reduced pressure. The residue was triturated with ether and the solid was collected and dried in vacuo to give the title compound (27.3 g, 92%). $^1$H NMR (360 MHz, CDCl$_3$) δ 7.82 (3H, m), 7.79 (1H, br s), 7.48 (2H, d, J 8.5 Hz), 7.23 (2H, m), and 2.30 (3H, s).

Description 28

5-Chloro-2-(4-chlorophenyl)-1-H-indole n-Butyllithium (1.6M in hexanes, 127 mL, 203 mmol) was added dropwise to a stirred, cooled (−10° C.) solution of 4-chloro-N-(4-chloro-2-methylphenyl)benzamide (Description 27, 27.1 g, 97 mmol) in tetrahydrofuran (600 mL). The mixture was allowed to warm to room temperature and stirred overnight. The mixture was cooled to 0° C. and further n-butyllithium (1.6M in hexanes, 30 mL, 483 mmol) was added dropwise. The mixture was stirred at room temperature for 2 h., then hydrochloric acid (2.5M, 200 mL) was added. The mixture was stirred at room temperature overnight, then extracted with ethyl acetate. The combined organic fractions were dried (MgSO$_4$) and the solvent was evaporated under reduced pressure. The residue was purified by flash column chromatography on silica gel, eluting with isohexane/EtOAc (85:15), to give the title compound (3.6 g, 14%). $^1$H NMR (360 MHz, CDCl$_3$) δ 8.30 (1H, br s), 7.57 (3H, m), 7.42 (2H, d, J 9.1 Hz), 7.30 (1H, d, J 8.6 Hz), 7.15 (1H, dd, J 8.6, 2.0 Hz) and 6.74 (1H, s).

Description 29

5-Methyl-2-(4-methylphenyl)-1H-benzimidazole

4-Methylbenzoyl chloride (2.17 mL, 2.54 g, 16.4 mmol) in dichloromethane (25 mL) was added dropwise to a stirred, cooled (0° C.) solution of 4-methyl-1,2-benzenediamine (2.0 g, 16.4 mmol) and triethylamine (4.57 mL, 3.32 g, 33 mmol) in dichloromethane (25 mL) and the mixture was stirred at room temperature overnight. The solvent was evaporated under reduced pressure, acetic acid (40 mL) was added and the mixture was stirred at 100° C. for 24 h. The solvent was evaporated under reduced pressure, water (100 mL) was added and the pH was adjusted to 7.0 with aqueous sodium carbonate (10%). Ethyl acetate (50 mL) was added, the layers were separated and the aqueous layer was extracted with ethyl acetate (4×35 mL). The combined organic fractions were washed with brine, dried (MgSO$_4$) and the solvent was evaporated under reduced pressure. The residue was dissolved in ethanol, heated to reflux and allowed to cool. The mixture was filtered and the solvent was evaporated under reduced pressure to give the title compound (1.17 g, 32%). $^1$H NMR (360 MHz, CDCl$_3$) δ 7.92 (2H, d, J 8.2 Hz), 7.52 (1H, d, J 8.1 Hz), 7.38 (1H, d, J 1.0 Hz), 7.27 (2H, d, J 8.2 Hz), 7.08 (1H, dd, J 8.1, 1.0 Hz), 2.47 (3H, s), and 2.40 (3H, s). m/z (ES$^+$) 223 (M+1).

Description 30

5-Chloro-2-(4-chlorophenyl)-1H-indole-3-propanoic acid

Triethylamine (5 mL, 3.6 g, 36 mmol) was added dropwise to a stirred suspension of 4-chloro-δ-oxobenzenepentanoic acid (7.91 g, 35 mmol) and (4-chlorophenyl)hydrazine hydrochloride (6.29 g, 35 mmol) in ethanol (54 mL) and the mixture was stirred at room temperature for 3 h. Ether (500 mL) was added, the mixture was filtered and the solvent was evaporated under reduced pressure. The residue was added slowly to trifluoroacetic acid (120 mL) and the mixture was heated under reflux for 2 h. The mixture was cooled, water (250 mL) was added and the mixture was extracted with ethyl acetate (300 mL). The organic fraction was washed with brine (30 mL), dried (MgSO$_4$) and the solvent was evaporated under reduced pressure. The residue was recrystallized from EtOAc/isohexane to give the title compound (7.6 g, 65%). $^1$H NMR (250 MHz, DMSO-d$_6$) δ 12.01 (1H, br s), 11.36 (1H, s), 7.56–7.47 (5H, m), 7.26 (1H, d, J 8.5 Hz), 7.01 (1H, dd, J 8.5, 2.0 Hz), 2.96 (2H, t, 8.0 Hz), and 2.43 (2H, t, 8.0 Hz).

Description 31

5-Chloro-2-(4-chlorophenyl)-1-methyl-1H-indole-3-propanoic acid

Sodium hydride (60% suspension in mineral oil, 5.98 g) was added in portions to a stirred, cooled (0° C.) solution of 5-chloro-2-(4-chlorophenyl)-1H-indole-3-propanoic acid (Description 30, 10 g, 30 mmol) in dimethylformamide (100 mL) and the mixture was stirred at 0° C. for 30 min. Iodomethane (9 mL) was added in one portion and the mixture was stirred at room temperature for 30 min. Water (1.5 L) was added and the mixture was extracted with ether (3×400 mL). The combined organic fractions were dried (MgSO$_4$) and the solvent was evaporated under reduced pressure. The residue was dissolved in methanol (240 mL) and aqueous sodium hydroxide (4M, 60 mL) was added. The mixture was heated under reflux for 1 h., cooled and the pH was adjusted to 1.0 with hydrochloric acid (2M). The layers were separated and the aqueous layer was extracted with ethyl acetate. The combined organic fractions were dried (MgSO$_4$) and the solvent was evaporated under reduced pressure. The residue was triturated with hexane and the solid was collected and dried in vacuo to give the title compound (7.5 g, 72%). $^1$H NMR (360 MHz, CDCl$_3$) δ 7.58 (1H, d, J 1.8 Hz), 7.44–7.48 (2H, m), 7.18–7.30 (4H, m), 3.53 (3H, s), 2.96–3.00 (2H, m), and 2.54–2.59 (2H, m).

Description 32

1-{3-[5-Chloro-2-(4-chlorophenyl)-1-methyl-1H-indol-3-yl]-1-oxopropyl}-4-(phenylmethyl)-4-piperidinol 1,1-Carbonyl diimidazole (47 mg, 0.29 mmol) was added to a solution of 5-chloro-2-(4-chlorophenyl)-1-methyl-1H-indole-3-propanoic acid (Description 31, 100 mg, 0.29 mmol) in tetrahydrofuran (4 mL) and the mixture was heated under reflux for 2 h. The mixture was cooled and 4-(phenylmethyl)-4-piperidinol (52 mg, 0.27 mmol) was added. The mixture was stirred at room temperature overnight and the solvent was evaporated under reduced pressure. Water (4 mL) was added and the mixture was stirred at 80° C. for 2 h. The mixture was cooled, the water was decanted and the residue was dissolved in dichloromethane.

Using a Bond Elut™ cartridge to separate the layers the solution was washed with hydrochloric acid (1M), and aqueous sodium hydroxide (2M). The organic fraction was evaporated under reduced pressure to a small volume and filtered through a plug of silica on a Bond Elut™ cartridge, eluting with hexane/EtOAc (85:15 increasing to 70:30), to give the title compound as a colorless solid (101 mg, 68%). $^1$H NMR (360 MHz, CDCl$_3$) δ 7.53 (1H, s), 7.40 (2H, d, J 6.5 Hz), 7.07–7.27 (9H, m), 4.29 (1H, m), 3.47 (3H, s), 3.29 (1H, m), 3.11 (1H, m), 2.90 (2H, m), 2.79 (1H, m), 2.59 (2H, s), 2.43 (2H, m), 1.52 (1H, br s), 1.40 (2H, m), 1.29 (1H, m), and 1.15 (1H, m). m/z (ES$^+$) 521, 523 (M+1). Found: C, 69.30; H, 5.82; N, 5.36. C$_{30}$H$_{30}$Cl$_2$N$_2$O$_2$ requires: C, 69.10; H, 5.80; N, 5.37%.

Description 33

1-{3-[5-Chloro-2-(4-chlorophenyl)-1H-indol-3-yl]-1-oxopropyl}-4-(2-methoxyphenyl)piperazine Prepared from 5-chloro-2-(4-chlorophenyl)-1H-indole-3-propanoic acid (Description 30) and 1-(2-methoxyphenyl)piperazine according to the method of Description 32. $^1$H NMR (250 MHz, CDCl$_3$) δ 8.04 (1H, br s), 7.61 (1H, d, J 1.8 Hz), 7.48 (4H, m), 7.29 (1H, d, J 8.5 Hz), 7.17 (1H, dd, J 8.5, 1.8 Hz), 7.02 (1H, m), 7.00–6.82 (3H, m), 3.86 (3H, s), 3.78 (2H, t, J 4.9 Hz), 3.46 (2H, t, J 4.9 Hz), 3.24 (2H, t, J 7.9 Hz), 2.94 (2H, t, J 4.9 Hz), 2.79 (2H, t, J 4.9 Hz), and 2.68 (2H, t, J 7.9 Hz). m/z (ES$^+$) 508, 510 (M+1).

Description 34

1-{3-[5-Chloro-2-(4-chlorophenyl)-1-methyl-1H-indol-3-yl]-1-oxopropyl}-4-(2-methoxyphenyl)piperazine Sodium hydride (60% suspension in mineral oil, 40 mg, 1 mmol) was added to a solution of 1-{3-[5-chloro-2-(4-chlorophenyl)-1H-indol-3-yl]-1-oxopropyl}-4-(2-methoxyphenyl)piperazine (Description 33, 270 mg, 0.53 mmol) in dimethylformamide (10 mL) and the mixture was stirred at room temperature for 10 min. Iodomethane (165 μl, 376 mg, 2.65 mmol) was added and the mixture was stirred at room temperature for 1 h. Water (100 mL) was added and the mixture was extracted with ether (2×40 mL). The combined organic fractions were washed with water (3×40 mL) and brine (40 mL), dried (MgSO$_4$) and the solvent was evaporated under reduced pressure to give the title compound as a beige foam. $^1$H NMR (360 MHz, CDCl$_3$) δ 7.60 (1H, d, J 1.7 Hz), 7.48 (2H, d, J 8.4 Hz), 7.32 (2H, d, J 8.4 Hz), 7.24 (1H, d, J 8.5 Hz), 7.20 (1H, dd, J 8.5, 1.7 Hz), 7.02 (1H, t, J 7.8 Hz), 6.94–6.82 (3H, m), 3.86 (3H, s), 3.75 (2H, t, J 5.0 Hz), 3.54 (3H, s), 3.40 (2H, t, J 5.0 Hz), 3.02 (2H, t, J 8.1 Hz), 2.95 (2H, t, J 5.0 Hz), 2.80 (2H, t, J 5.0 Hz), and 2.55 (2H, t, J 8.1 Hz). m/z (ES$^+$) 522, 524 (M+1).

Example 1

1-{3-[5-Chloro-2-(4-chlorophenyl)-1-methyl-1H-pyrrolo[2,3-b]pyridine-3-yl]-1-oxopropyl}-4-(phenylmethyl)-4-piperidinol Lithium hydroxide monohydrate (15 mg, 0.34 mmol) was added to a solution of methyl 5-chloro-2-(4-chlorophenyl)-1-methyl-1H-pyrrolo[2,3-b]pyridine-3-propanoate (Description 5, 82 mg, 0.23 mmol) in methanol (15 mL), tetrahydrofuran (5 mL) and water (5 mL) and the mixture was stirred at room temperature overnight. Further lithium hydroxide monohydrate (15 mg, 0.34 mmol) was added and the mixture was stirred at 75° C. for 2 h. The solvent was evaporated under reduced pressure and the residue was dissolved in tetrahydrofuran (25 mL). 1-Hydroxybenzotriazole (549 mg, 1.84 mmol), triethylamine (255 μl, 1.84 mmol), 1-(3-dimethylaminopropyl)-3-ethylcarbodiimide hydrochloride (348 mg, 1.84 mmol) and 4-(phenylmethyl)-4-piperidinol (352 mg, 1.84 mmol) were added and the mixture was stirred at room temperature overnight. The mixture was poured into water and extracted with ethyl acetate. The combined organic fractions were washed with hydrochloric acid (1M), aqueous sodium carbonate (10%) and brine, dried (MgSO$_4$) and the solvent was evaporated under reduced pressure. The residue was purified by flash column chromatography on silica gel, eluting with isohexane/EtOAc (50:50), to give the title compound (98 mg, 83%). $^1$H NMR (360 MHz, CDCl$_3$) δ 8.28 (1H, d, J 2.2 Hz), 7.90 (1H, d, J 2.2 Hz), 7.27–7.48 (2H, m), 7.36–7.26 (5H, m), 7.16–7.14 (2H, m), 4.36 (1H, m), 3.65 (3H, s), 3.36 (1H, m), 3.19 (1H, m), 3.00 (2H, m), 2.86 (1H, m), 2.67 (2H, s), 2.48 (2H, t, J 7.7 Hz), 1.46 (2H, m), 1.39 (1H, m), and 1.22 (1H, m). m/z (ES$^+$) 522, 524 (M+1).

Example 2

1-{3-[5-Chloro-2-(4-chlorophenyl)-1-methyl-1H-pyrrolo[2,3-c]pyridine-3-yl]-1-oxopropyl}-4-(phenylmethyl)-4-piperidinol Prepared from methyl 5-chloro-2-(4-chlorophenyl)-1-methyl-1H-pyrrolo[2,3-c]pyridine-3-propanoate (Description 10) according to the method of Example 1. $^1$H NMR (360 MHz, CDCl$_3$) δ 8.49 (1H, s), 7.52 (3H, m), 7.34–7.25 (5H, m), 7.16 (2H, d, J 7.4 Hz), 4.35 (1H, m), 3.63 (3H, s), 3.40 (1H, m), 3.22 (1H, m), 2.96 (2H, m), 2.87 (1H, m), 2.70 (2H, s), 2.48 (2H, t, J 7.9 Hz), and 1.54–1.26 (4H, m). m/z (ES$^+$) 522, 524 (M+1).

Example 3

1-{3-[2-(4-chlorophenyl)-1-methyl-1H-pyrrolo[3,2-c]pyridine-3-yl]-1-oxopropyl}-4-(phenylmethyl)-4-piperidinol Prepared from methyl 2-(4-chlorophenyl)-1-methyl-1H-pyrrolo[3,2-c]pyridine-3-propanoate (Description 13) according to the method of Example 1. $^1$H NMR (400 MHz, CD$_3$OD) δ 9.70 (1H, s), 8.24 (1H, d, J 5.9 Hz), 7.58 (2H, d, J 8.5 Hz), 7.49 (1H, d, J 5.9 Hz), 7.45 (2H, d, J 8.5 Hz), 7.28–7.14 (5H, m), 4.18 (1H, m), 3.61 (3H, s), 3.38 (1H, m), 3.12 (1H, m), 3.04 (2H, m), 2.82 (1H, m), 2.65 (2H, m), 2.58 (2H, s), and 1.42–0.88 (4H, m. m/z (ES$^+$) 488, 490 (M+1).

Example 4

1-{3-[5-Chloro-2-(4-chlorophenyl)-1-methyl-1H-pyrrolo[3,2-b]pyridine-3-yl]-1-oxopropyl}-4-(phenylmethyl)-4-piperidinol Prepared from methyl 5-chloro-2-(4-chlorophenyl)-1-methyl-1H-pyrrolo[3,2-b]pyridine-3-propanoate (Description 16) according to the method of Example 1. $^1$H NMR (360 MHz, CDCl$_3$) δ 7.54 (1H, d, J 8.5 Hz), 7.49 (2H, d, J 8.4 Hz), 7.38 (2H, d, J 8.4 Hz), 7.30 (3H, m), 7.17 (2H, d, J 7.4 Hz), 7.13 (1H, d, J 8.5 Hz), 4.30 (1H, m), 3.79 (1H, m), 3.57 (3H, s), 3.32 (1H, m), 3.04 (2H, t, J 8.1 Hz), 2.88 (2H, m), 2.79 (1H, m), 2.73 (2H, s), and 1.51 (4H, m). m/z (ES$^+$) 522,524 (M+1).

Example 5

1-{3-[6-Chloro-2-(4-chlorophenyl)imidazo[1,2-a]pyridine-3-yl]-1-oxopropyl}-4-(phenylmethyl)-4-piperidinol Sodium borohydride (30 mg, 0.8 mmol) was added to a solution of (E)-1-{3-[6-chloro-2-(4-chlorophenyl)imidazo

[1,2-a]pyridine-3-yl}-1-oxo-2-propenyl}-4-(phenylmethyl)-4-piperidinol (Description 20, 40 mg, 0.08 mmol) in pyridine/methanol (3:1, 4 mL) and the mixture was stirred under reflux for 2 h. Further portions of sodium borohydride (30 mg, 0.8 mmol) were added and the reaction was monitored by mass spectrometry until no starting material remained. The mixture was cooled, poured into water (75 mL) and extracted with ethyl acetate (3×25 mL). The combined organic fractions were washed with brine, dried (MgSO$_4$) and the solvent was evaporated under reduced pressure. The residue was purified by flash column chromatography on silica gel, eluting with isohexane/EtOAc (35:65). The residue was recrystallised from ethanol/water and the solid was collected and dried in vacuo to give the title compound as a colorless solid. $^1$H NMR (360 MHz, CDCl$_3$) δ 8.18 (1H, d, J 1.5 Hz), 7.74 (2H, d, J 8.5 Hz), 7.56 (1H, d, J 9.6 Hz), 7.44 (2H, d, J 8.5 Hz), 7.30 (3H, m), 7.15 (3H, m), 4.40 (1H, m), 3.47 (2H, m), 3.43 (1H, m), 3.24 (1H, m), 2.92 (1H, m), 2.68 (2H, s), 2.64 (2H, t, J 7.5 Hz), 1.46 (2H, m), and 1.24 (2H, m). m/z (ES$^+$) 508, 510 (M+1).

Example 6

1-{3-[6-Methyl-2-(4-methylphenyl)imidazo[1,2-a]pyridine-3-yl]-1-oxopropyl}-4-(2-methoxyphenyl)piperazine Prepared from (E)-1-{3-[6-methyl-2-(4-methylphenyl)-imidazo[1,2-a]pyridine-3-yl]-1-oxo-2-propenyl}-4-(2-methoxyphenyl)piperazine (Description 24) according to the method of Example 5. $^1$H NMR (360 MHz, CDCl$_3$) δ 7.88 (1H, s), 7.70 (2H, d, J 8.4 Hz), 7.56 (1H, d, J 8.1 Hz), 7.27 (2H, d, J 8.4 Hz), 7.02 (2H, m), 6.93–6.81 (3H, m), 3.85 (3H, s), 3.78 (2H, t, J 5.0 Hz), 3.51 (2H, t, J 7.6 Hz), 3.42 (2H, t, J 5.0 Hz), 2.91 (2H, t, J 5.0 Hz), 2.76 (2H, t, J 5.0 Hz), 2.70 (2H, t, J 7.6 Hz), 2.40 (3H, s), and 2.37 (3H, s). m/z (ES$^+$) 469 (M+1).

Example 7

1-{3-[6-Chloro-2-(4-fluorophenyl)-1H-indol-1-yl]-1-oxopropyl}-4-(2-methoxyphenyl)piperazine A mixture of 6-chloro-2-(4-fluorophenyl)-1H-indole (Description 26, 348 mg, 1.4 mmol), 4-(2-methoxyphenyl)-1-(1-oxo-2-propenyl)piperazine (Description 25, 400 mg, 1.6 mmol) and potassium carbonate (1.5 g, 10.8 mmol) in dimethylformamide was stirred at 100° C. for 48 h. The mixture was cooled and aqueous ammonium chloride (saturated, 10 mL) and water (30 mL) were added. The mixture was extracted with ethyl acetate and the combined organic fractions were dried (MgSO$_4$) and the solvent was evaporated under reduced pressure. The residue was purified by flash column chromatography on silica gel, eluting with isohexane/EtOAc (50:50), to give the title compound. $^1$H NMR (360 MHz, CDCl$_3$) δ 7.51 (1H, d, J 8.4 Hz), 7.45 (3H, m), 7.18 (2H, t, J 8.7 Hz), 7.11 (1H, dd, J 8.4, 1.8 Hz), 7.01 (1H, m), 6.93–6.81 (3H, m), 6.48 (1H, s), 4.51 (2H, t, J 7.7 Hz), 3.85 (3H, s), 3.72 (2H, t, J 5.0 Hz), 3.30 (2H, t, J 5.0 Hz), 2.93 (2H, t, J 5.0 Hz), 2.79 (2H, t, J 5.0 Hz), and 2.56 (2H, t, J 7.7 Hz). m/z (ES$^+$) 492, 494 (M+1).

Example 8

1-{3-[5-Chloro-2-(4-chlorophenyl)-1H-indol-1-yl]-1-oxopropyl}-4-(2-methoxyphenyl)piperazine Prepared from 5-chloro-2-(4-chlorophenyl)-1H-indole (Description 28) according to the method of Example 7. $^1$H NMR (360 MHz, CDCl$_3$) δ 7.58 (1H, d, J 2.0 Hz), 7.47 (2H, d, J 8.6 Hz), 7.42 (2H, d, J 8.6 Hz), 7.36 (1H, d, J 8.7 Hz), 7.20 (1H, dd, J 8.7, 2.0 Hz), 7.02 (1H, t, J 7.6 Hz), 6.92 (1H, t, J 7.6 Hz), 6.86 (1H, d, J 7.6 Hz), 6.81 (1H, d, J 7.6 Hz), 6.48 (1H, s), 4.56 (2H, t, J 7.6 Hz), 3.85 (3H, s), 3.70 (2H, t, J 5.0 Hz), 3.26 (2H, t, J 5.0 Hz), 2.89 (2H, t, J 5.0 Hz), 2.75 (2H, t, J 5.0 Hz), and 2.53 (2H, t, J 7.6 Hz). m/z (ES$^+$) 508, 510 (M+1).

Example 9

1-{3-[5-Methyl-2-(4-methylphenyl)-1H-benzimidazol-1-yl]-1-oxopropyl}-4-(2-methoxyphenyl)piperazine, and 1-{3-[6-Methyl-2-(4-methylphenyl)-1H-benzimidazol-1-yl]-1-oxopropyl}-4-(2-methoxyphenyl)piperazine Prepared as a 1:1 mixture from 5-methyl-2-(4-methylphenyl)-1H-benzimidazole (Description 29) according to the method of Example 7. $^1$H NMR (360 MHz, CDCl$_3$) δ 7.69–7.60 (3H, m), 7.35–7.24 (3H, m), 7.13 (1H, m), 7.01 (1H, m), 6.91–6.80 (3H, m), 4.65 (2H, m), 3.85 (3H, s), 3.73 (2H, m), 3.34 (2H, m), 2.92 (2H, m), 2.85–2.65 (4H, m), 2.53, 2.49 (Total 3H, each s) and 2.43 (3H, s). m/z (ES$^+$) 469 (M+1).

Example 10

(2RS-cis)- and (2RS-trans)-1-{3-[5-Chloro-2-(4-chlorophenyl)-2,3-dihydro-1-methyl-1H-indol-3-yl]-1-oxopropyl}-4-(phenylmethyl)-4-piperidinol Sodium cyanoborohydride (126 mg, 2 mmol) was added to a solution of 1-{3-[5-chloro-2-(4-chlorophenyl)-1-methyl-1H-indol-3-yl]-1-oxopropyl}-4-(phenylmethyl)-4-piperidinol (Description 32, 100 mg, 0.2 mmol) in trifluoroacetic acid (4 mL) and the mixture was stirred at room temperature for 15 min. The solvent was evaporated under reduced pressure and aqueous sodium hydrogen carbonate was added. The mixture was extracted with ethyl acetate (2×30 mL) and the combined organic fractions were washed with brine, dried (MgSO$_4$) and the solvent was evaporated under reduced pressure. The residue was purified by flash column chromatography on silica gel, eluting with isohexane/EtOAc (50:50) to give the title compound as a brown foam (100 mg, 96%). $^1$H NMR (360 MHz, CDCl$_3$) 85:15 mixture of cis- and trans- isomers δ 7.35–7.04 (11H, m), 6.48 (0.85H, d, J 8.3 Hz), 6.39 (0.15H, d, J 8.3 Hz), 4.49 (0.85H, d, J 8.4 Hz), 4.29 (1H, m), 3.97 (0.15H, d, J 9.7 Hz), 3.40–3.16 (3H, m), 2.87 (1H, m), 2.74 (1.7H, s), 2.72 (0.45H, s), 2.59 (2.55H, s), 2.52 (0.3H, s), 2.09 (2H, m), and 1.55–1.29 (6H, m).

Example 11

(2RS-cis)-1-{3-[5-Chloro-2-(4-chlorophenyl)-2,3-dihydro-1-methyl-1H-indol-3-yl]-1-oxopropyl}-4-(2-methoxyphenyl)piperazine Sodium cyanoborohydride (180 mg, 2.9 mmol) was added to a solution of 1-{3-[5-chloro-2-(4-chlorophenyl)-1-methyl-1H-indol-3-yl]-1-oxopropyl}-4-(2-methoxyphenyl)piperazine (Description 33, 150 mg, 0.29 mmol) in trifluoroacetic acid (4 mL) and the mixture was stirred at room temperature for 1 h. The solvent was evaporated under reduced pressure and aqueous sodium hydrogen carbonate was added. The mixture was extracted with ethyl acetate (2×40 mL) and the combined organic fractions were washed with brine, dried (MgSO$_4$) and the solvent was evaporated under reduced pressure. The residue was purified by flash column chromatography on silica gel, eluting with isohexane/EtOAc (50:50) to give a mixture of (2RS-cis)-1-{3-[5-chloro-2-(4-chlorophenyl)-2,3-dihydro-1-methyl-1H-indol-3-yl]-1-oxopropyl}-4-(2-methoxyphenyl)piperazine and (2RS-trans)-1-{3-[5-chloro-2-(4-chlorophenyl)-2,3-dihydro-1-methyl-1H-indol-3-yl]-1-oxopropyl}-4-(2-methoxyphenyl)piperazine (120 mg, 80%). A sample (50 mg) was purified by MPLC chromatography on silica gel, eluting with isohexane/EtOAc (50:50) to give (2RS-cis)-1-{3-[5-chloro-2-(4-chlorophenyl)-2,3-dihydro-1-methyl-1H-indol-3-yl]-1-oxopropyl}-4-(2-methoxyphenyl)piperazine (18 mg); $^1$H NMR (360 MHz, CDCl$_3$) δ 7.32 (4H, m), 7.12–6.87 (6H, m), 6.48 (1H, d, J 8.3 Hz), 4.50 (1H, d, J 8.3 Hz), 3.87 (3H, s), 3.71 (2H, m), 3.34 (3H, m), 2.88 (4H, m), 2.59 (3H, s), 2.21 (2H, m), and 1.62–1.38 (4H, m); and (2RS-trans)-1-{3-[5-chloro-2-(4-chlorophenyl)-2,3-dihydro-1-methyl-1H-indol-3-yl]-1-oxopropyl}-4-(2-methoxyphenyl)piperazine (0.7 mg); $^1$H NMR (360 MHz, CDCl$_3$) δ 7.34 (4H, m), 7.12–6.87 (6H, m), 6.40 (1H, d, J 8.3 Hz), 3.99 (1H, d, J 9.7 Hz), 3.88 (3H, s), 3.76 (2H, t, J 5.0 Hz), 3.46 (2H, t, J 5.0 Hz), 3.23 (1H, m), 2.97 (4H, m), 2.54 (3H, s), and 2.38–2.00 (4H, m).

What we claim is:

1. A compound of the formula (I):

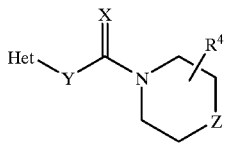

I wherein:

Het represents a heterocyclic residue selected from:

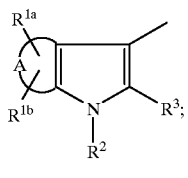

(a)

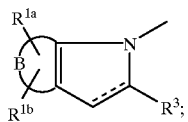

(b)

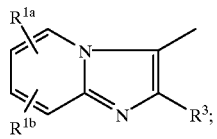

(c)

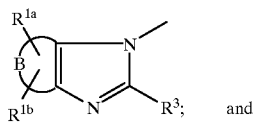

(d)

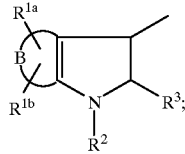

(e)

where the dotted line in (b) represents an optional double bond;

A completes a fused pyridine ring;

B completes a fused benzene or pyridine ring;

X represents an oxygen atom, a sulfur atom, two hydrogen atoms, =NH or =N(C$_{1-6}$alkyl);

Y is a straight or branched C$_{1-4}$alkylene chain optionally substituted by halogen, oxo or hydroxy; or Y represents a straight or branched C$_{2-4}$alkenylene or C$_{2-4}$alkynylene chain;

Z represents CR$^5$R$^6$ so as to complete a piperidine ring;

R$^{1a}$ and R$^{1b}$ each independently represent hydrogen, C$_{1-6}$alkyl, C$_{2-6}$alkenyl, C$_{1-6}$alkoxy, fluoroC$_{1-6}$alkyl, fluoroC$_{1-6}$alkoxy, halogen, cyano, NR$^a$R$^b$, SR$^a$, SOR$^a$, SO$_2$R$^a$, OSO$_2$R$^a$, NR$^a$COR$^b$, COR$^a$, CO$_2$R$^a$ or CONR$^a$R$^b$;

R$^2$ represents hydrogen, C$_{1-6}$alkyl, fluoroC$_{1-6}$alkyl, (CH$_2$)$_m$ COR$^a$, (CH$_2$)$_p$CO$_2$R$^a$, (CH$_2$)$_p$OH, (CH$_2$)$_m$ CONR$^a$R$^b$, (CH$_2$)$_m$phenyl or SO$_2$C$_{1-6}$alkyl;

R$^3$ represents phenyl, biphenyl, naphthyl or heteroaryl, wherein said phenyl, biphenyl, naphthyl or heteroaryl group may be optionally substituted by one, two or three groups independently selected from halogen, C$_{1-6}$alkyl, C$_{1-6}$alkoxy, fluoroC$_{1-6}$alkyl, fluoroC$_{1-6}$ alkoxy, NO$_2$, cyano, SR$^a$, SOR$^a$, SO$_2$R$^a$, COR$^a$, CO$_2$R$^a$, CONR$^a$R$^b$, C$_{2-6}$alkenyl, C$_{2-6}$alkynyl, C$_{1-4}$alkoxyC$_{1-4}$alkyl or —O(CH$_2$)$_{1-2}$O—;

R$^4$ represents hydrogen, methyl, carbonyl, benzyl, or a methylene bridge across the 2,5-positions on the piperadine ring;

R$^5$ and R$^6$ each independently represent hydrogen, halogen, C$_{1-6}$alkyl, C$_{3-7}$cycloalkyl, C$_{3-7}$cycloalkylC$_{1-4}$ alkyl, C$_{2-6}$alkenyl, cyano, naphthyl, fluorenyl, (CH$_2$)$_m$ phenyl, (CH$_2$)$_m$heteroaryl, CH(phenyl)$_2$, CH(C$_{1-6}$ alkyl)(phenyl), C(C$_{1-6}$alkyl)(phenyl)$_2$, CO(phenyl), C(OH)(phenyl)$_2$, C$_{2-4}$alkenyl(phenyl), (CH$_2$)$_m$NR$^c$R$^d$, (CH$_2$)$_p$CONR$^c$R$^d$, (CH$_2$)$_p$NR$^a$COR$^b$, (CH$_2$)$_m$COR$^c$, (CH$_2$)$_m$CO$_2$R$^c$ or (CH$_2$)$_m$OH wherein said phenyl, naphthyl, fluorenyl or heteroaryl groups may be optionally substituted by one, two or three groups independently selected from halogen, C$_{1-6}$alkyl, C$_{1-6}$alkoxy, fluoroC$_{1-6}$alkyl, fluoroC$_{1-6}$alkoxy, NO$_2$, cyano, SR$^a$, SOR$^a$, SO$_2$R$^a$, COR$^a$, CO$_2$R$^a$, CONR$^a$R$^b$, C$_{2-6}$alkenyl, C$_{2-6}$alkynyl, C$_{1-4}$alkoxyC$_{1-4}$alkyl or —O(CH$_2$)$_{1-2}$O—;

or R$^5$ and R$^6$ together are linked so as to form a 5- or 6-membered ring optionally substituted by =O, =S or a C$_{1-4}$alkyl or hydroxy group, and optionally containing a double bond, which ring may optionally contain in the ring one or two heteroatoms selected from O and S, or groups selected from NR$^c$, SO or SO$_2$, and to which ring there is either fused or attached a benzene or thiophene ring, which benzene or thiophene ring is optionally substituted by 1, 2 or 3 substituents selected from C$_{1-6}$alkyl, C$_{3-7}$cycloalkyl, C$_{3-7}$cycloalkylC$_{1-4}$ alkyl, phenylC$_{1-4}$alkyl, trifluoromethyl, cyano, OR$^a$, SR$^a$, SOR$^a$, SO$_2$R$^a$, NR$^a$R$^b$, NR$^a$COR$^b$, NR$_a$CO$_2$R$^b$, NR$^a$SO$_2$R$^b$, COR$^a$, CO$_2$R$^a$ or CONR$^a$R$^b$, wherein the phenyl moiety of a phenylC$_{1-4}$alkyl group may be substituted by C$_{1-6}$alkyl, C$_{1-6}$alkoxy, halogen or trifluoromethyl;

R$^a$ and R$^b$ each independently represents hydrogen, C$_{1-4}$alkyl, fluoroC$_{1-4}$alkyl or phenyl; or the group —NR$^a$R$^b$ may form a 5- or 6-membered ring optionally substituted by =O, =S or a C$_{1-4}$alkyl or hydroxy group, and optionally containing a double bond, which ring may optionally contain in the ring one or two heteroatoms selected from O and S, or groups selected from NR$^c$, SO or SO$_2$;

R$^c$ and R$^d$ each independently represents hydrogen, C$_{1-4}$alkyl, fluoroC$_{1-4}$alkyl, C$_{2-4}$alkenyl, COR$^a$, SO$_2$R$^a$, phenyl or benzyl or R$^c$ and R$^d$, together with the nitrogen atom to which they are attached, form a heteroaliphatic ring of 4 to 7 atoms, to which ring there may optionally be fused a benzene ring;

m is zero or an integer from 1 to 4;

p is an integer from 1 to 4;

or a pharmaceutically acceptable salt thereof.

2. A compound according to claim 1 wherein R$^{1a}$ and R$^{1b}$ each independently represent hydrogen, halogen, C$_{1-6}$alkyl, C$_{2-6}$alkenyl, fluoroC$_{1-6}$alkoxy, NR$^a$R$^b$, COR$^a$, CO$_2$R$^a$, or heteroaryl.

3. A compound according to claim 2 wherein R$^{1a}$ and R$^{1b}$ each independently represent hydrogen, methyl, vinyl, trifluoromethoxy, fluorine, chlorine, bromine, pyrrolidinyl, piperidinyl, morpholino, acetyl, methoxycarbonyl, pyridyl or furyl.

4. A compound according to claim 3 wherein R$^{1a}$ represents methyl or chloro, and R$^{1b}$ is hydrogen.

5. A compound according to claim 1 wherein R$^{1a}$ is attached to the 5-position when Het represents (a) or (e), to the 5- or 6-position when Het represents (b) or (d), and to the 6-position when Het represents (c).

6. A compound according to claim 1 wherein Het represents (a) or (e) and R$^2$ represents hydrogen, C$_{1-6}$alkyl, fluoroC$_{1-6}$alkyl, (CH$_2$)$_m$COR$^a$, (CH$_2$)$_p$COR$^a$, (CH$_2$)$_p$OH or (CH$_2$)$_m$phenyl.

7. A compound according to claim 6 wherein R$^2$ represents C$_{1-3}$alkyl, fluoroC$_{1-3}$alkyl, COCH$_3$, CH$_2$CO$_2$H, CH$_2$CO$_2$CH$_3$, (CH$_2$)$_{1-2}$OH (especially CH$_2$CH$_2$OH) or benzyl.

8. A compound according to claim 7 wherein R$^2$ is hydrogen or methyl.

9. A compound according to claim 1 wherein R$^3$ represents phenyl, biphenyl, naphthyl or heteroaryl wherein said phenyl, biphenyl, naphthyl or heteroaryl group is optionally substituted by one or two groups selected from halogen, C$_{1-6}$alkyl, C$_{1-6}$alkoxy, trifluoroC$_{1-6}$alkyl, fluoroC$_{1-6}$alkoxy or C$_{2-6}$alkenyl.

10. A compound according to claim 9 wherein R$^3$ represents phenyl, biphenyl, naphthyl or heteroaryl wherein said phenyl, biphenyl, naphthyl or heteroaryl group is optionally substituted by one or two groups selected from fluorine, chlorine, bromine, C$_{1-4}$alkyl, methoxy, trifluoromethyl, trifluoromethoxy or vinyl.

11. A compound according to claim 10 wherein R$^3$ represents 2-pyridyl, 3-pyridyl or phenyl optionally substituted by one or two groups selected from fluorine, chlorine, bromine, C$_{1-4}$alkyl, methoxy, trifluoromethyl, trifluoromethoxy or vinyl.

12. A compound according to claim 11 wherein R$^3$ represents phenyl, 4-methylphenyl, 4-chlorophenyl, 4-bromophenyl, 4-fluorophenyl, 2-pyridyl or 3-pyridyl.

13. A compound according to claim 1 wherein R$^4$ is hydrogen.

14. A compound according to claim 1 wherein Z represents CR$^5$R$^6$, wherein

R$^5$ represents halogen, C$_{3-7}$cycloalkyl, C$_{3-7}$cycloalkylC$_{1-4}$alkyl, phenyl, heteroaryl, (CH$_2$)$_p$phenyl, (CH$_2$)$_p$heteroaryl, CH(phenyl)$_2$, CH(C$_{1-6}$alkyl)(phenyl), C(C$_{1-6}$alkyl)(phenyl)$_2$, CO(phenyl), C(OH)(phenyl)$_2$, or (CH$_2$)$_p$NR$^c$R$^d$, wherein said phenyl or heteroaryl group is optionally substituted by one or two substituents selected from halogen, C$_{1-6}$alkyl, C$_{1-6}$alkoxy, fluoroC$_{1-6}$alkyl, fluoroC$_{1-6}$alkoxy, NO$_2$, cyano, SR$^a$ or —O(CH$_2$)$_{1-2}$O—; and R$^6$ represents hydrogen, fluorine, cyano, (CH$_2$)$_m$NR$^c$R$^d$, (CH$_2$)$_p$NR$^a$COR$^b$, (CH$_2$)$_m$CO$_2$R$^c$ or (CH$_2$)$_m$OH, where R$^a$, R$^b$, R$^c$ and R$^d$ are as defined in claim 1.

15. A compound as claimed in claim 14 wherein R$^5$ represents C$_{5-7}$cycloalkyl, phenyl, heteroaryl, (CH$_2$)$_p$phenyl, CO(p-methoxyphenyl), C(OH)(phenyl)$_2$, or (CH$_2$)$_p$NR$^c$R$^d$, wherein each of said phenyl or heteroaryl groups may be substituted by one or two groups independently selected from halogen, C$_{1-4}$alkyl, C$_{1-4}$alkoxy, fluoroC$_{1-4}$alkyl, fluoroC$_{1-4}$alkoxy, NO$_2$, cyano and SO$_2$R$^a$, or said phenyl or heteroaryl group may be substituted by the group —O(CH$_2$)$_{1-2}$O—.

16. A compound according to claim 14 wherein R$^6$ represents hydrogen, fluorine, cyano, (CH$_2$)$_m$NR$^c$R$^d$, (CH$_2$)$_p$NR$^a$COR$^b$, (CH$_2$)$_m$CO$_2$R$^c$ or (CH$_2$)$_m$OH.

17. A compound according to claim 1 wherein R$^5$ and R$^6$ are so linked as to form a 5- or 6-membered ring, such that said CR$^5$R$^6$ moiety is selected from:

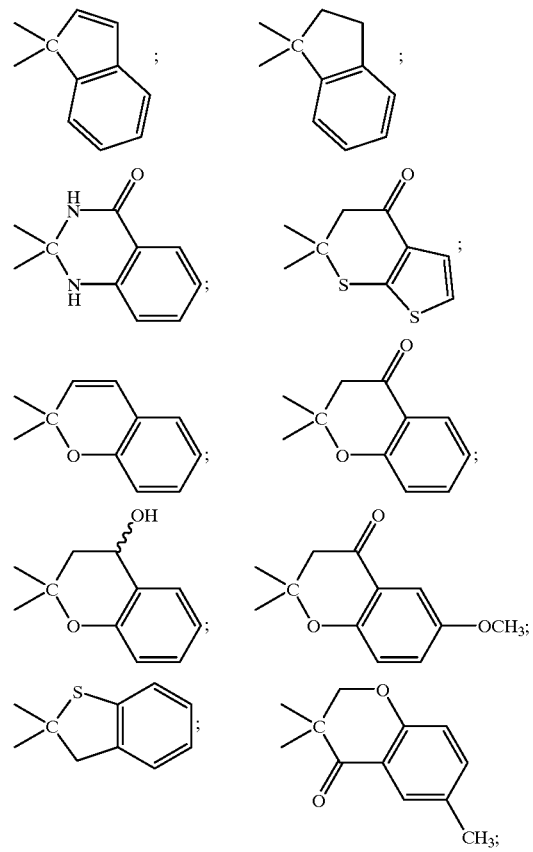

-continued

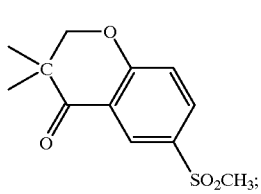 and 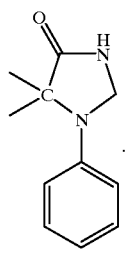

18. A compound according to claim 17 wherein said $CR^5R^6$ moiety is selected from:

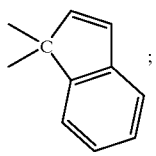 ; 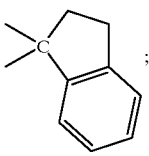 ;

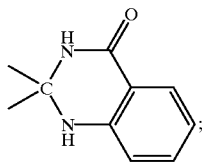 ; 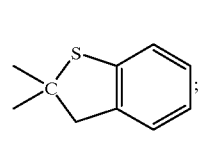 ;

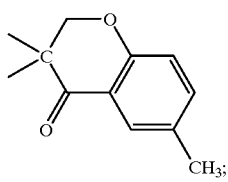

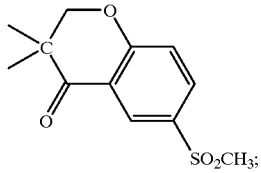 and 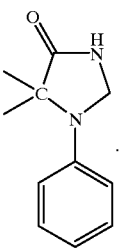.

19. A compound according to claim 1 wherein X represents an oxygen atom, two hydrogen atoms, or =NH.

20. A compound according to claim 19 wherein X is an oxygen atom.

21. A compound according to claim 1 wherein Y is —CH$_2$CH$_2$—, —CH$_2$CH(CH$_3$)—, —CH=CH— or —C≡C—.

22. A compound according to claim 21 wherein Y is —CH$_2$CH$_2$—.

23. A compound according to claim 1 wherein X is two hydrogen atoms and Y is —CH$_2$CH$_2$—, —CH$_2$C(O)—, —CH$_2$CHOH— or —CH$_2$CHF—.

24. A compound according to claim 1 of the formula (Ia):

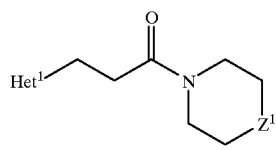

(Ia)

wherein Het$^1$ represents a residue selected from:

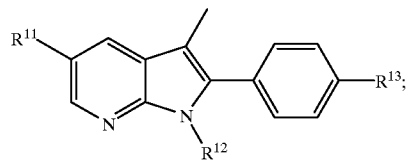

(a1)

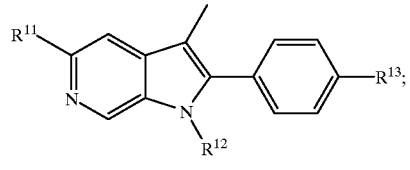

(a2)

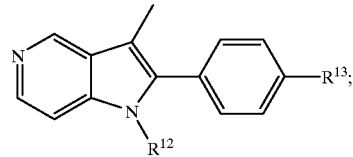

(a3)

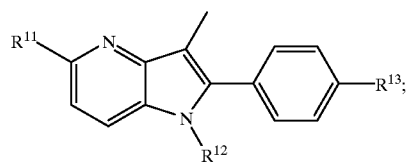

(a4)

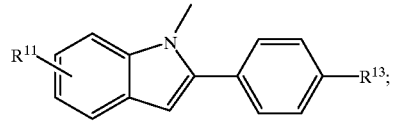

(b1)

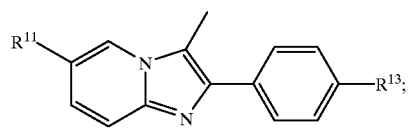

(c1)

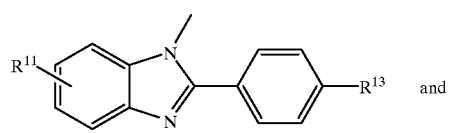 and (d1)

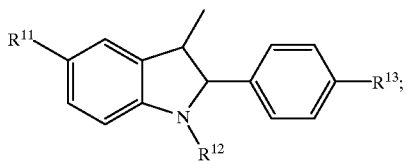

(e1)

$Z^1$ represents $CR^{15}R^{16}$;

$R^{11}$ represents hydrogen, chlorine or methyl, and when $Het^1$ represents (b1) or (d1), $R^{11}$ is in the 5-position or the 6-position;

$R^{12}$ represents a hydrogen atom or a group selected from $C_{1-3}$alkyl, fluoro$C_{1-3}$alkyl, $COCH_3$, or $(CH_2)_2OH$;

$R^{13}$ represents a halogen atom or a group selected from $C_{1-4}$alkyl, $C_{2-4}$alkenyl, fluoro$C_{1-4}$alkyl, $C_{1-4}$alkoxy or fluoro$C_{1-4}$alkoxy;

$R^{15}$ represents cyclohexyl, phenyl, 2-indolyl, $CH_2$phenyl, $CH_2CH_2$phenyl, CO(p-methoxyphenyl), C(OH)(phenyl)$_2$, $NR^cR^d$ or $CH_2NR^cR^d$ (where $R^c$ and $R^d$ each independently represent hydrogen, methyl, $COCH_3$, $COCH_2CH_3$, $SO_2CH_3$ or phenyl, or $R^c$ and $R^d$, together with the nitrogen atom to which they are attached, form a piperidine ring) and wherein each phenyl group is optionally substituted by one or two substituents selected from fluorine, chlorine, bromine, methyl, methoxy, trifluoromethoxy or $SO_2CH_3$;

$R^{16}$ represents hydrogen, fluorine, cyano, $NR^cR^d$ (where $R^c$ and $R^d$ each independently represent hydrogen or methyl), $NHCOCH_3$, $CH_2NHCOCH_3$, $CO_2H$, $CO_2CH_3$, OH or $CH_2OH$;

or $R^{15}$ and $R^{16}$ together are so linked as to form a 5- or 6-membered ring optionally substituted by =O, and optionally containing a double bond, which ring optionally contains in the ring an oxygen or sulfur atom or 1 or 2 NH groups, and to which ring is either fused or attached a benzene ring, which benzene ring is optionally substituted by methyl or $SO_2CH_3$.

25. A compound according to claim 24 wherein $R^{12}$ represents hydrogen, methyl, $COCH_3$ or —$(CH_2)_2OH$.

26. A compound according to claim 24 wherein $R^{13}$ represents chlorine, bromine, fluorine, methyl, ethyl, isopropyl, trifluoromethyl or vinyl.

27. A compound according to claim 24 wherein $Z^1$ represents $CR^{15}R^{16}$; $R^{15}$ represents cyclohexyl, phenyl, benzyl, 4-chlorophenyl, 3-trifluoromethylphenyl, NH(phenyl), N(CH$_3$)(phenyl) or N(COCH$_2$CH$_3$)(phenyl); and $R^{16}$ represents hydrogen, fluorine, hydroxy or $CO_2CH_3$.

28. A compound selected from:
   1-{3-[5-chloro-2-(4-chlorophenyl)-1-methyl-1H-pyrrolo[2,3-b]pyridine-3-yl]-1-oxopropyl}-4-(phenylmethyl)-4-piperidinol;
   1-{3-[5-chloro-2-(4-chlorophenyl)-1-methyl-1H-pyrrolo[2,3-c]pyridine-3-yl]-1-oxopropyl}-4-(phenylmethyl)-4-piperidinol;
   1-{3-[2-(4-chlorophenyl)-1-methyl-1H-pyrrolo[3,2-c]pyridine-3-yl]-1-oxopropyl}-4-(phenylmethyl)-4-piperidinol;
   1-{3-[5-chloro-2-(4-chlorophenyl)-1-methyl-1H-pyrrolo[3,2-b]pyridine-3-yl]-1-oxopropyl}-4-(phenylmethyl)-4-piperidinol;
   1-{3-[6-chloro-2-(4-chlorophenyl)imidazo[1,2-a]pyridine-3-yl]-1-oxopropyl}-4-(phenylmethyl)-4-piperidinol;
   (2RS-cis)-1-{3-[5-chloro-2-(4-chlorophenyl)-2,3-dihydro-1-methyl-1H-indol-3-yl]-1-oxopropyl}-4-(phenylmethyl)-4-piperidinol;
   (2RS-trans)-1-{3-[5-chloro-2-(4-chlorophenyl)-2,3-dihydro-1-methyl-1H-indol-3-yl]-1-oxopropyl}-4-(phenylmethyl)-4-piperidinol;

or a pharmaceutically acceptable salt thereof.

29. A pharmaceutical composition comprising a compound as claimed in claim 1, together with at least one pharmaceutically acceptable carrier or excipient.

* * * * *